United States Patent [19]
Scanlon

[11] Patent Number: 5,853,005
[45] Date of Patent: *Dec. 29, 1998

[54] ACOUSTIC MONITORING SYSTEM

[75] Inventor: Michael V. Scanlon, Silver Spring, Md.

[73] Assignee: The United States of America as represented by the Secretary of the Army, Washington, D.C.

[*] Notice: The term of this patent shall not extend beyond the expiration date of Pat. No. 5,515,865.

[21] Appl. No.: 643,139

[22] Filed: May 2, 1996

[51] Int. Cl.$^6$ ............................ A61B 8/14; H04R 25/00; A61H 1/00; B23P 19/02

[52] U.S. Cl. ................................ 128/662.03; 128/663.01; 128/660.61; 128/660.02; 600/25; 601/2; 601/46; 601/47; 601/55; 381/150; 381/166; 29/235.5; 5/83.1

[58] Field of Search ................. 128/660.01, 660.02, 128/660.03, 660.04, 660.05, 660.08, 660.09, 660.1, 661.04, 661.08, 662.01, 662.03, 663.01; 600/25; 601/2, 46, 47, 48, 49, 55, 56, 57; 381/150, 166; 29/235.5; 5/250.1, 83.1, 85.1, 69.5, 413, 417, 690; 340/573

[56] References Cited

U.S. PATENT DOCUMENTS

| | | |
|---|---|---|
| Re. 32,180 | 6/1986 | Lewiner et al. . |
| 3,547,106 | 12/1970 | Bornmann . |
| 3,972,320 | 8/1976 | Kalman . |
| 4,146,885 | 3/1979 | Lawson, Jr. . |
| 4,366,533 | 12/1982 | Wettach ................................... 340/573 |
| 4,407,293 | 10/1983 | Suarez, Jr. et al. ..................... 128/660 |
| 4,438,771 | 3/1984 | Friesen et al. . |
| 4,619,270 | 10/1986 | Margolis et al. . |
| 4,630,614 | 12/1986 | Atlas . |
| 4,694,839 | 9/1987 | Timme . |
| 4,722,346 | 2/1988 | Chen ........................................ 128/660 |
| 4,813,427 | 3/1989 | Schlaefke et al. . |
| 4,862,144 | 8/1989 | Tao . |
| 5,515,865 | 5/1996 | Scanlon . |
| 5,532,681 | 7/1996 | Peters et al. ............................. 340/573 |
| 5,557,263 | 9/1996 | Fisher et al. ............................. 340/573 |
| 5,559,497 | 9/1996 | Hong ....................................... 340/573 |
| 5,581,238 | 12/1996 | Chang et al. ............................ 340/573 |

OTHER PUBLICATIONS

Monitoring of Breathing with a Segmetnal Air–Filed Mattress J. Gundersen and K. Dahlin, Med & Biol Engng, vol. 9, p. 541 Pergamon Press 1971, Printed in Great Britain.

*Primary Examiner*—Mickey Yu
*Assistant Examiner*—Dinh X. Nguyen
*Attorney, Agent, or Firm*—Paul S. Clohan, Jr.; William Eshelman; Mark Kelly

[57] ABSTRACT

A transducer in communication with fluid in a pad held in close contact against a sound or movement source monitors acoustic signals transferred into the fluid. The signal pattern is monitored aurally and/or compared to predetermined reference patterns, and optional control and stimulation means can be activated in response to the comparison results. The sensed acoustic signal can be transmitted to a remote receiver or processed locally. Typically, the acoustic signal is representative of the heartbeat or breathing of a living organism. The monitoring system may be applied to diverse situations including SIDS, apnea, home baby monitoring, medical transport devices, blood pressure cuffs, seats, combat casualty care and hand-held devices.

96 Claims, 12 Drawing Sheets

ACOUSTIC MONITORING SYSTEM

BACKGROUND OF THE INVENTION

1. Field of the Invention

The present invention relates to a sound and movement monitor suitable for detecting activity and, more particularly, to a sound and movement monitor suitable for providing the capability to locally or remotely monitor living organism body functions.

2. Discussion of the Related Art

The acoustic signatures of various body functions, such as heart rate, pulmonary function, respiration, etc., provide valuable input to the medical caregiver in diagnosing medical conditions and monitoring responses to changed circumstances and treatments. Moreover, patterns of such acoustic activity can be used to identify the presence or even the onset of reduced physical ability or condition and concurrently, mental alertness. Anticipation of such conditions can allow intervention to avoid hazardous situations resulting from diminished capacity, as for instance, in the operation of motor vehicles and heavy machinery.

Several problems have hampered efforts to effect practical systems that would perform ongoing biological monitoring with and without feedback stimulation. In many environments the ambient noise renders airborne transmission of pertinent signals ineffective. Moreover, airborne coupling mechanisms, such as conventional stethoscopes, are insufficiently efficient to provide the necessary definition and distinction between competing acoustic pulses. On the other hand, invasive monitoring techniques such as implants and fixed-position transducers are too inconvenient and uncomfortable for widespread application.

Accordingly, there exists in the prior art a long felt need for a passive non-invasive acoustic and movement monitor suitable for simply and remotely providing body function monitoring, particularly one easily adaptable to providing biofeedback stimulation to the monitored organism.

SUMMARY OF THE INVENTION

It is accordingly one object of the present invention to overcome the above mentioned disadvantages of the prior art and to monitor biological activity of a living organism using an improved acoustic monitoring system.

It is a further object of the present invention to acquire a signal corresponding to the acoustic activity or movement of a living organism and to transmit that signal to a remote receiver.

It is yet another object of the present invention to provide an acoustic monitoring system which produces an output signal corrected for ambient noise.

It is another object of the present invention to provide an acoustic monitoring system having multiple transducers for providing signal directional information.

It is also an object of this invention to provide an acoustic monitoring system having a sensor pad formable to the contours of support surfaces.

An acoustic monitoring system in accordance with the present invention includes a fluid-filled sensor pad adapted to conform to at least a portion of the surface of a living organism and acoustic transducing means for monitoring and converting acoustic signals received by the pad into electrical signals corresponding to the acoustic signals.

The "transducing means" can be any type of sensor or transducer, where by "transducer" is meant a microphone or similar means for picking up acoustic signals (e.g., heartbeat) and/or varying pressure signals. For example, the transducer could be a vibratory and/or movement sensor, such as an accelerometer, a strain gage, an optical displacement sensor, or a fiber-optic sensor. Chemical, biological, and electrical emission sensors could also be used as a transducer to indicate the condition of the object in accordance with the present invention.

The transducer output, in accordance with the preferred embodiment, can be transmitted to a remote location and monitored by audio and visual indicators of sensor activity. Respiratory, pulmonary, digestive, and vocalized sounds transduced can be recreated at the remote monitor, or transmitted to medical personnel for diagnosis and treatment. A remote station could be configured to monitor one or several sensor pads simultaneously, and selectively choose to monitor each of the transducer's audio output.

A stimulator can also be provided to generate vibratory, oscillatory or shaking movement of the fluid within the pad. If provided, the stimulator also can generate an audible noise to stimulate the object acoustically, or a light source to stimulate the object visually. Additionally, electrical, chemical, mechanical, or other energy sources could be used as a stimulator.

The sensor pad preferably has characteristics sufficient to transmit to the transducer the movement from the object in the form of at least one of breathing, heart and motion sounds of the object. The shape and performance features of the pad will be tailored to each application, such as for use in a crib, cuff, vehicle seat, or gurney. The sensor pad and transducer could also be built into existing products. In a preferred embodiment, the sensor pad is liquid-filled with a pressure transducer arranged in communication with the internal volume of the pad such that forces applied to the pad by the object cause pressure changes which are detected by the pressure transducer. The pressure transducer provides an output proportional to the pressure changes, and preferably can also discriminate between the physical presence and absence of an object placed upon the sensor pad.

The sensor pad may be a bladder or pouch having sidewall surfaces sufficiently rigid to readily transmit pressure fluctuations from the object to the transducer. These surfaces should allow acoustic signals to be transmitted through the walls, facilitating communication between the object, fluid medium, and transducer.

The invention may further comprise an alarm selectively activated by the monitoring system when the output from the transducer corresponds to preselected movement or sound patterns from the object such as the onset of measurable symptoms indicative of certain conditions, such as falling asleep, snoring, or choking.

Still other objects and advantages of the present invention will become readily apparent to those skilled in this art from the following detailed description, wherein only the preferred embodiments of the invention are shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

DESCRIPTION OF THE PREFERRED EMBODIMENT

Figure 1:
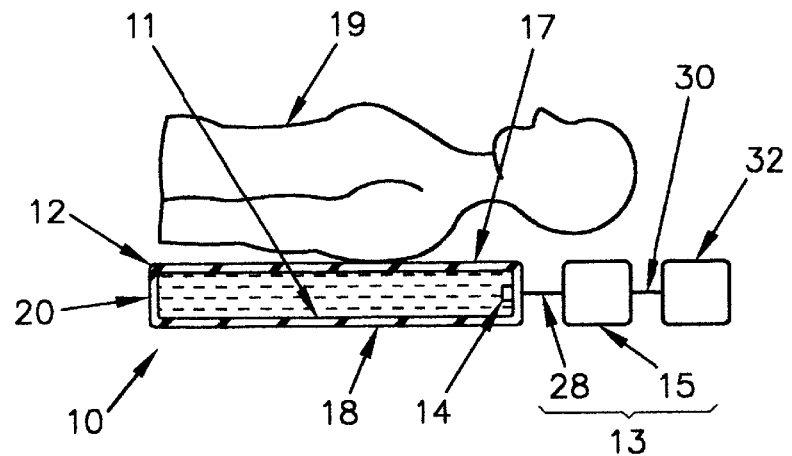
FIG. 1 is an illustration, partly in schematic form, of an acoustic monitoring system according to the present invention.
Figure 2:
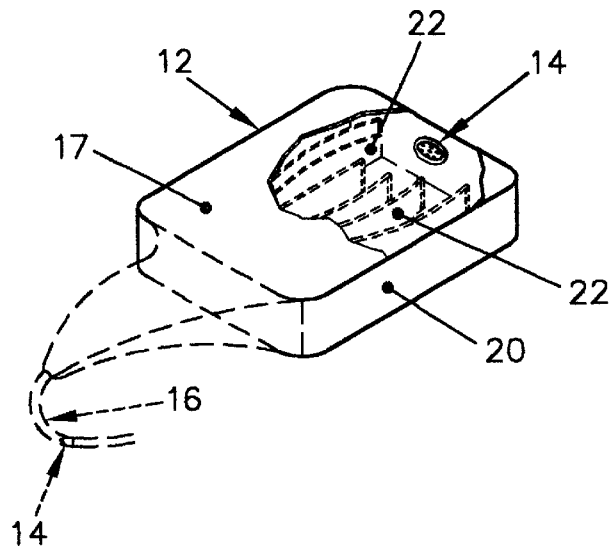
FIG. 2 is a perspective view, partly in section, of an exemplary sensor pad that may be used to practice the present invention.

An acoustic monitoring system 10 according to the present invention, as shown in FIGS. 1 and 2, includes a sensor pad 12 defining a fluid-filled chamber 11 and a sensing and monitoring system 13 including an acoustic pressure transducer 14 acoustically coupled with the chamber and a signal processing and output system 15 for processing output signals from the transducer caused by pressure fluctuations in the pad such as may be caused by biological activity of a living organism 19 in contact with the pad.

Sensor pad 12 is shown as a generally flat bladder having opposed, generally rectangular top and bottom walls 17 and 18 and side walls 20 transversely connecting peripheral edges of the top and bottom walls to define the chamber therebetween. The dimensions of the sensor pad are dependent upon the available area for the specific application and on maximizing the acoustical contact between the pad and the organism. For example, the size or dimension of the pad could be as large as a person's torso, small enough to perform pinpoint (localized) acoustic observations on a joint, or miniaturized to be swallowed. The pad can be formed of any suitable material including, but not limited to, plastic and rubber materials, but is preferably formed of a polychloroprene rubber, which has a characteristic of becoming acoustically transparent when submerged in water (as simulated by sandwiching the material between a human body and an appropriate fluid within the pad). Portions of the pad which contact the organism should have good sound transmission properties without absorbing the acoustic pressure fluctuations of interest; however, the pad may also have portions or surfaces specifically intended to prevent transmission from other acoustic sources not intended for monitoring. The rigidity of the walls of the sensor pad must also facilitate acoustic transmission without being flexible enough to conform to a patient's face so as not to restrict breathing.

Chamber 11 is preferably filled with a fluid such as water to provide superior acoustic coupling between the pad and a living organism such as a human body, which is mostly water, thereby improving signal-to-noise ratio over ambient sounds and allowing medical personnel to detect sounds which are often difficult to discern, such as fluid in the lungs, an obstructed airway, or an irregular heart beat. Other fluids that can be used include saline solution, oil, alcohol, thicksotropic fluids such as aerogels and gels or any other suitable materials which will couple well with a living organism and transmit acoustical signals adequately. Thicksotropic materials, that is, materials which do not flow under their own weight but which are easily deformed, will also dampen fluid oscillations resulting from motion or vibration.

Acoustic transducer 14 is shown mounted in a side wall of the sensor pad but can be mounted, suspended or carried in any position on or within the sensor pad so long as it is acoustically coupled with the fluid. The transducer is preferably a piezoelectric, electret, or condenser-based hydrophone, similar to those used by Navy in sonar applications, but can be any other type of suitable waterproof pressure and motion sensing type of sensor. Utilization of an instrumentation grade hydrophone allows collection of calibrated wide band acoustic data since hydrophones can have a flat omni-directional frequency response from less than about 1 Hz to about 160 kHz with excellent sensitivity and durability. Frequency response of the transducer and pad design can be tailored for anticipated acoustic targets. For example, the majority of the frequency content of human physiological sounds is in the range of 10 to 400 Hz, however, acoustic information exists in the infrasonic (below the typical 20 Hz limit of normal hearing) and ultrasonic (above 20 kHz) regions. Infrasonic sounds cannot be detected by human ears, regardless of the amplitude, but a hydrophone with infrasonic response can detect these signals, and the information can be presented to the listener by either visual methods or frequency translation schemes that shift infrasonic sounds into the audible region, if desired.

Figure 9:
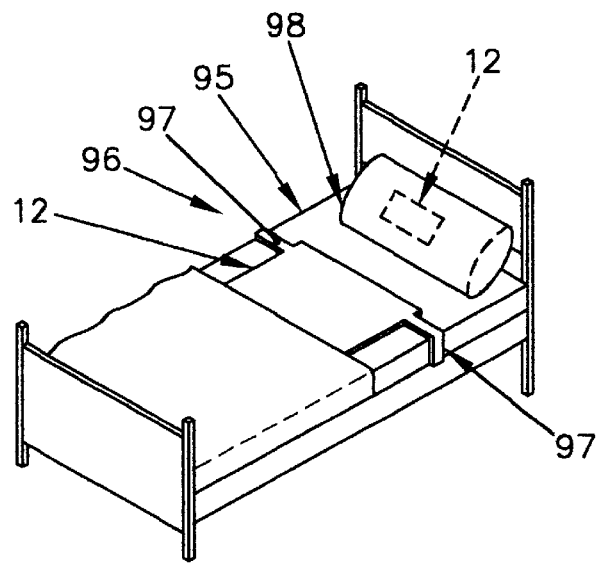
FIG. 9 is a perspective view of a bed and pillow each provided with acoustic monitoring systems according to the present invention.

The signal processing and output system 15 receives an output signal 28 from transducer 14, processes the signal and provides an output 30. System 15 is preferably battery-operated and may, for example, be identical or similar to the circuitry disclosed in applicant's co-pending U.S. patent applications Ser. No. 08/292,441, filed Aug. 17, 1994 now abandoned and Ser. No. 08/231,081, filed Apr. 22, 1994, now U.S. Pat. No. 5,515,865, the disclosures of which are incorporated herein by reference. Other circuitry which may be used is disclosed in FIGS. 9 and 11 of U.S. Pat. No. 4,862,144, the disclosure of which is also incorporated herein by reference. The above-mentioned circuits deal primarily with baby monitoring and stimulation techniques for Sudden Infant Death Syndrome (SIDS), apnea or general monitoring of people placed on a pad. Other types of signal processing can include broad-band amplification, narrow band filtering, variable gain, automatic gain control (AGC), use of an adaptive filter for noise cancellation, neural net identification, FFT or wavelet-based analysis or decomposition, joint time frequency analysis, voice processing, transfer functioning correlation techniques, template matching, beam-forming algorithms, level detection (with threshold), timing measurements, harmonic analysis, use of decision trees, comparison with a data base and auto-calibration. Output 30 can be fed to a post-processing unit 32, such as a speaker or head-set, a transmitter for remote monitoring, a display showing data from the sensor or analyzed data or conclusions, storage media or post-processing system, local and/or remote indicators using sound, light, radio frequency signals or mechanical indication, or a reaction mechanism for stimulating, resuscitating, shocking, notifying or paging the living organism or alerting a caretaker. Output 30 can also be connected to most data acquisition systems, such as analog or digital audio tape recorders, strip charts or computer acquisition boards to record not just the occurrence of physiological events but tonal and temporal qualities as well. The transducer 14 and signal processor and output system 15 should be battery operated to remove any chance of electrocution; however, AC power sources can be used if appropriate electrical isolation is ensured.

In use, pad 12 is filled with a fluid medium such as water and is made to support or contact a living organism or animate object such as the human body shown in FIG. 1 at 19. When filled with a fluid having acoustical properties similar to that of the organism, the pad acts as a fluid extension of the organism to function as an acoustical conduit or extension to transducer 14 within the pad thereby enabling the transducer to collect high signal-to-noise ratio acoustic signals generated by the organism. In the case of a human body, this may allow medical personnel to detect sounds which are often difficult to discern, such as fluid in the lungs, an obstructed airway or an irregular heart beat. Generally, fluctuations in the fluid associated with acoustics or motion of the body will be converted to a voltage output by transducer 14. The electrical output of the transducer can then be filtered, amplified, analyzed and/or transmitted by system 13, depending upon the specific application. Acoustical analysis of the sensor pad output provides amplitude, phase, frequency, duration, rate and correlative information that may be useful for medical diagnosis, patient care and research, and such analysis may be performed in the field, in transit or at a medical facility. Traditional diagnostic methods such as listening to an audio output and looking at a voltage-versus-time waveform can be augmented by joint time-frequency domain analysis techniques, neural networks, wavelet based techniques or template matching, for example. In addition, sensed acoustic signals may be used to aid in diagnosis and may be compared to a database of acoustic signatures or to past experience, either locally or via telemedical monitoring systems.

Effective attenuation of unwanted ambient background noise results from the poor coupling between the airborne noise and the fluid-filled pad. In addition, acoustical and vibration isolation can be implemented in the sensor pad using materials like lead, foam, voids, absorber materials, acoustic gasket, suspension structures and anechoic materials. External and internal coatings, baffles and isolators can be configured to make certain areas of the sensor pad more sensitive to the acoustic target or body, and can help reject those sounds that may interfere with the diagnosis. When applied on the inner or outer surfaces of the pad, absorptive or anechoic materials can reduce reflections and selectively limit transmission to the fluid from various directions.

Heater elements with thermostats can be incorporated into the sensor pad, but should be electrically isolated and in a safe location. Thermoelectric coolers, heaters, warm or cold fluid flow (circulation like chillers or hot water heater), or evaporative cooling could also be implemented.

Aural interpretation of the sensor output and acoustic signature analysis can indicate cessation of breathing or heart beat, or other conditions, such as a partially obstructed airway, sucking chest wound, hyperventilation, asthma, murmurs, or can be used to detect subtle attributes of the acoustic signature that may not be noticed by auscultation or merely viewing the sensor's voltage-versus-time output. Sensor output may also be used to predict or diagnose disease or medical conditions such as epileptic seizures, heart attack, apnea, SIDS, or other conditions that may have some acoustic signature that is modified before, during, or after occurrence. Advance signal-processing techniques can enhance the signature through filtering or array processing, can determine the proper level of response for the indicated condition, and can alert attendants via transmitter or alarm that immediate attention or resuscitation is necessary. This information can be transmitted by various methods to other personnel or hardware for remote diagnosis, verification, data logging or additional signal processing, and can be used to supplement diagnostic equipment such as EEG, EKG, ECG, MRI, CT, scanners, Doppler echocardiogram, or other invasive or non-invasive technologies. By simultaneously monitoring acoustics with other forms of medical analysis equipment, the pad can provide a new dimension in patient care and research, for example, being able to both see and hear a heart valve closing, or to simultaneously view and listen to the sounds of an injured knee or ankle in motion.

Transducer 14 can be disposed within fluid-filled chamber 11 as shown or can be located a predetermined distance from the chamber and communicated with the chamber via a fluid-filled conduit or the like extending from the chamber as shown by broken lines in FIG. 2 at 16. In addition, the sensor pad can be formed with internal structures or partitions, as shown by broken lines in FIG. 2 at 22, to maintain the shape of the pad and to prevent complete constriction, as well as to define acoustic conduits which facilitate acoustic sensing by transmitting pressure fluctuations efficiently to the pressure transducer 14. Partitions 22 can be straight or curved and preferably extend upwardly from bottom wall 18 to terminate at an upper edge vertically spaced from top wall 17 when the sensor pad is not in use. It will be appreciated, however, that the partitions can depend downwardly from the top wall or that some of the partitions can extend upwardly from the bottom wall while others depend downwardly from the top wall, as desired.

Figure 3:
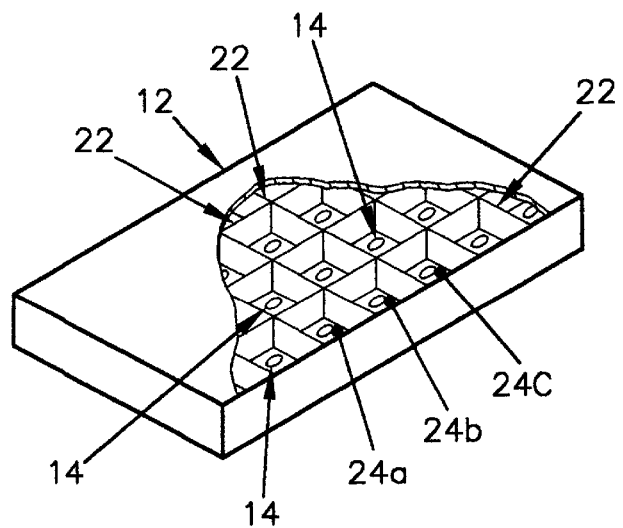
FIG. 3 is a perspective view, partly in section, of another exemplary sensor pad that may be used to practice the present invention.

Partitions 22 can also be used to define multiple chambers within the pad, as shown in FIG. 3 at 24a, 24b, 24c, etc., each with a transducer 14 disposed therein or in communication therewith. In this manner, a plurality of transducers can be placed within the pad for focused or sectional monitoring, wherein each of the transducers is monitored individually or selectively or a combined output is monitored. The walls or partitions can be formed of an acoustically insulative material to prevent internal chambers of the pad from communicating with one another or the walls can be acoustically transparent. The data from each individual transducer can be used to assess signal strength and time-of-arrival at various positions in the body, or origin of sound source, or to remove interfering noise sources such as the mother's heartbeat when trying to listen to a fetal heartbeat. More than one transducer can be employed using various array and noise canceling techniques. Issues such as signature complexity, cost, available area and application purpose will help determine whether arrays or single transducers would perform better, and how the signal should be processed.

Figure 4:
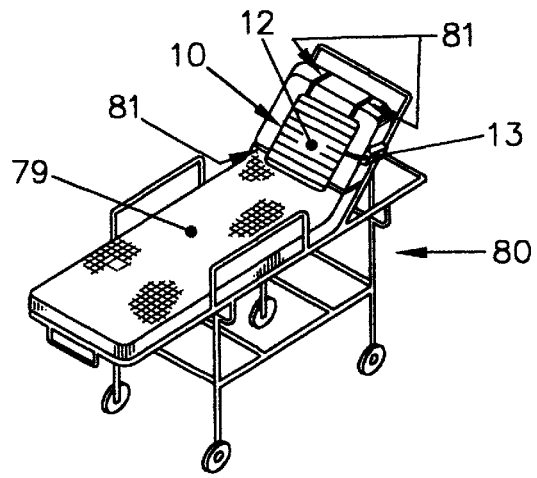
FIG. 4 is a perspective view of an acoustic monitoring system according to the present invention installed on a medical gurney.
Figure 5:
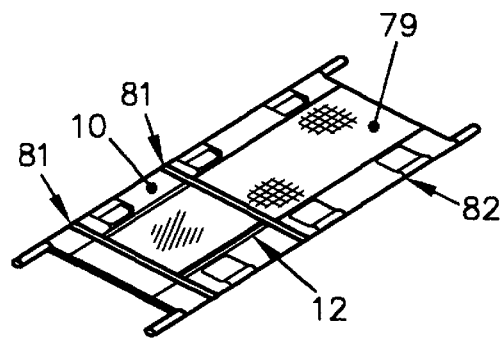
FIG. 5 is a perspective view of an acoustic monitoring system according to the present invention installed on a stretcher.
Figure 6:
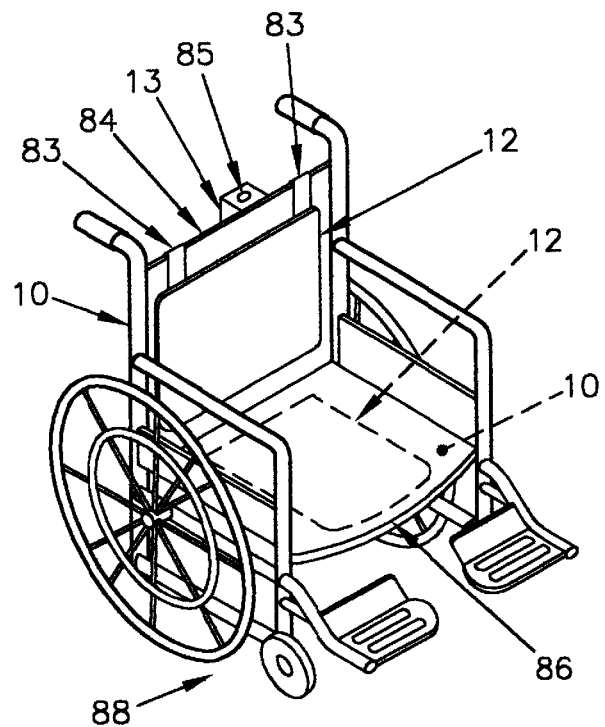
FIG. 6 is a perspective view of an acoustic monitoring system according to the present invention installed on a wheel chair.
Figure 7:
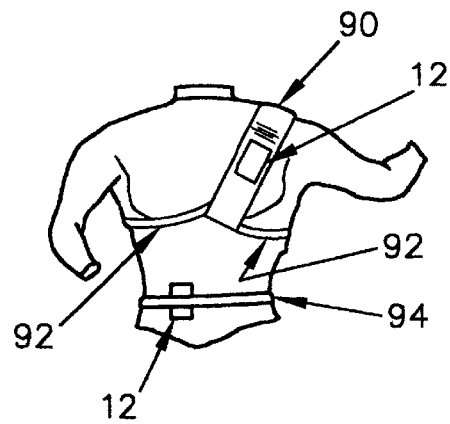
FIG. 7 is a fragmentary view of a human torso with acoustic monitoring systems applied to the chest with a shoulder strap and a second monitor applied to the abdomen with a belt.
Figure 8:
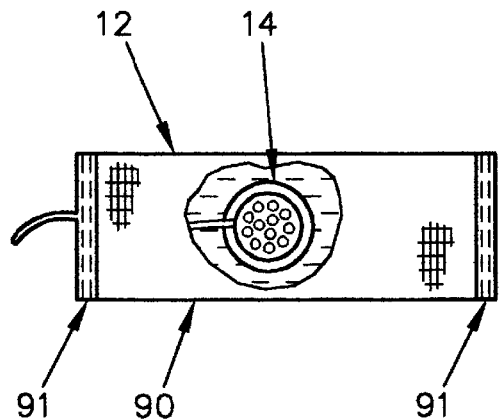
FIG. 8 is a plan view of the chest-mounted sensor pad of FIG. 7.

The sensor pad of the acoustic monitoring system according to the present invention can be carried on or built into a body support surface of any type of medical transport device such as, for example, a gurney, an evacuation stretcher, or a wheel chair. In FIG. 4, for example, a sensor pad 12 is configured to be attached across the top or support surface 79 of a gurney 80 using straps or bands 81 that wrap around the support surface. A transmitter, battery, electronic circuitry and other components of the acoustic monitoring system can be attached to the straps or the gurney close to the sensor as shown schematically at 13 in FIG. 4. A stretcher 82 is shown in FIG. 5 with a sensor pad 12 attached across the top or support surface 79 using straps or bands 81; and, in FIG. 6, a wheelchair 88 is shown having a back support 84 and seat 86 with a sensor pad 12 attached across the back support using clips 83. Alternatively, or in addition to providing a sensor pad on the back support, a sensor pad 12 can be attached to the seat 86 as shown by broken lines in FIG. 6. Monitoring components 13 of the system can also include an earphone jack or receptacle 85 to permit medical evaluation simply by inserting a headphone jack or plug (not shown) into the receptacle. The sensor pad can be permanently attached, removably attached or integrally formed with the support surface of the medical transport device to support any portion of the body of a patient or casualty while simultaneously providing vital life function information to care-provider personnel. A sensing pad according to the present invention can also be positioned directly on a hospital operating table or, alternatively, the pad can be made portable and be placed on an injured soldier's torso to immediately and continuously monitor heartbeat and breathing, fluid in the lungs, an obstructed airway, or an irregular heartbeat. In this regard, a sensor pad 12 could be incorporated into a blanket or an attachable pad 90 formed, for example, of a soft rubber tube clamped or glued at opposite ends to form seams 91 and filled with a sound conducting fluid as shown in FIGS. 7 and 8. Adjustable straps 92 or a belt 94 can be attached to pads as shown in order to urge the pads into acoustic transfer contact with the body and electronics attached to the pads, straps or belt can provide processing and output. Individual lengths or segments of tubing can be connected together using inserts or other mechanisms that create a fluid seal with the tubing when adjustable lengths are desired, for example to create a tube-like pad that can be wrapped around the neck, torso, arms, wrist or legs. Mobile army surgical hospital (MASH) units, field hospitals, and disaster response medical sites would obviously benefit from a monitor that could be placed under or against each patient of a full ward, each of whom could be selectively monitored, or have their pad provide an audible alarm when breathing or heart beating stops, for example. The low-cost of such a system makes it ideally suited for naval medical hospital ships, mobile army surgical hospitals, disaster sites, or any other location requiring a large number of monitors. Evacuation of injured personnel could use the present invention to monitor vital statistics. Since the device is passive and does not emit any form of energy, unlike ultrasonic, MRI, and X-ray monitoring, it is safe for long term and continuous monitoring for physiological disorders or indications, such as epileptic seizure onset, gastrointestinal diseases, neuromuscular disorders, and muscle spasms, fatigue, or recovery.

It will also be appreciated that hospital critical care units and nurseries can use the acoustical monitoring pad in incubators, bassinets, cradles, and cribs with heating pads built into the device for neonatal monitoring. Placing the infants on acoustic monitoring pads could be an effective way to obtain medical information without the tedious and painful attachment of leads.

The present invention could be attached to home or institution mattresses for health monitoring, recovery, research, or presence detection. In addition to medical applications, there may also be sleeping disorder benefits. For example, in FIG. 9, a bed 96 and pillow 98 are shown, each optionally equipped with sensor pads 12 according to the present invention mounted on body support surfaces. The bed-mounted fluid-filled pad 12 is shown mounted on a mattress 95 using straps 97 that wrap around the mattress and can be used to detect heartbeats, breaths, vocalizations, presence, snoring, apnea or be used for long term research or monitoring of epileptic seizure studies and gastrointestinal function. Pillow 98 can include a conventional core with a pad 12 disposed around part or all of the core or, alternatively, the pad can constitute the core of the pillow with foam or rubber cavities being optionally disposed therein to maintain shape and comfort. If internal foam is provided, it must adequately conduct sound or be positioned so that sound will travel through the fluid medium to the transducer. The pillow sensor thus formed can detect breath sounds, snoring, and possible heartbeat from blood vessels, arteries or veins in the head. Stimulation can also be applied, depending on the acoustics detected. Pleasing sounds or vibrations can be introduced to the pad or pillow to comfort, soothe or help induce sleep. For example, REM sleep (rapid eye movement) may be indicated by certain breathing and heart rates. Conditions in the pad, room, or bed, such as noise levels, sound content, temperature, bed stiffness, and air circulation could be modified in response to the monitored signals to enhance or help initiate the REM condition. Waterbeds could also be incorporated with an acoustic monitoring sensor to vary the conditions of the mattress in relation to the acoustical content of the monitored heart and breathing sounds.

Figure 10:
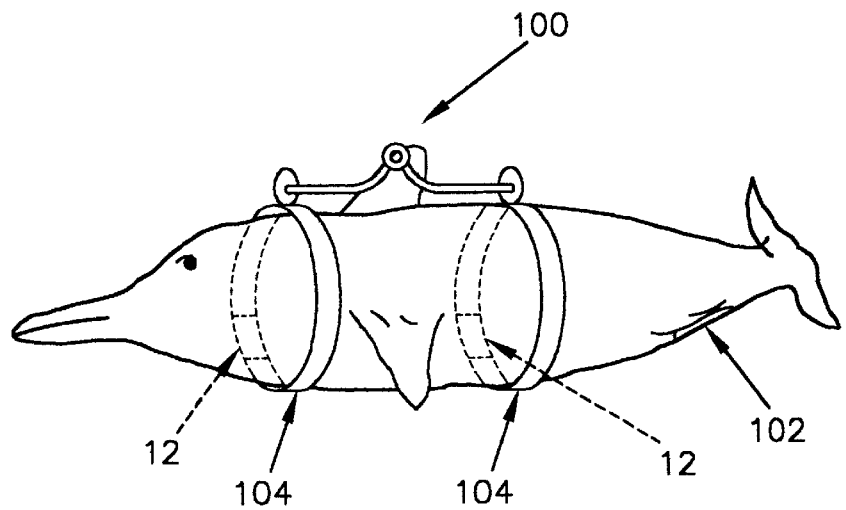
FIG. 10 is a perspective view of an animal lift mechanism equipped with sensor pads according to the present invention.

The sensor pad according to the present invention can be incorporated into lift, support, and sling mechanisms to assist in movement or transportation of people or animals. For example, in FIG. 10, sensor pads 12 are shown attached to straps or bands 104 which form a sling for transporting an animal 102. Bands 104 wrap around the animal to hold the sensor pads in tight contact with the animal surface as it is lifted. Alternatively, each band itself may define a fluid-filled chamber with a transducer disposed therein and thereby function as a sensor pad in accordance with the present invention. In the latter case, for example, the band can be formed of a kevlar sleeve to define a fluid-filled bladder or pad 12 with a transducer 14 being disposed within the bladder. Kevlar could be the load bearing structure yet still allow some acoustic coupling with the animal or person. The bands can be adjustable for various size animals and sensor location can be adjustable on the bands. The band materials require strength, water-proofing and good acoustic properties for the mammal, reptile or other animal requiring transport.

Recovering patients at home or other health care facility can be outfitted with a sensor pad that monitors heartbeat and breath rates, and an alarm or stimulator mechanism can be used on the patient if necessary, so that they know they have exceeded some preset limit of their doctor's advised exercise levels. Additionally, in the event of a heartbeat or breath cessation, either "911" or a doctor could be paged. Paging mechanisms with vibrators or beepers can also alert patients to be still while torso contact microphone data collection takes place.

Figure 11:
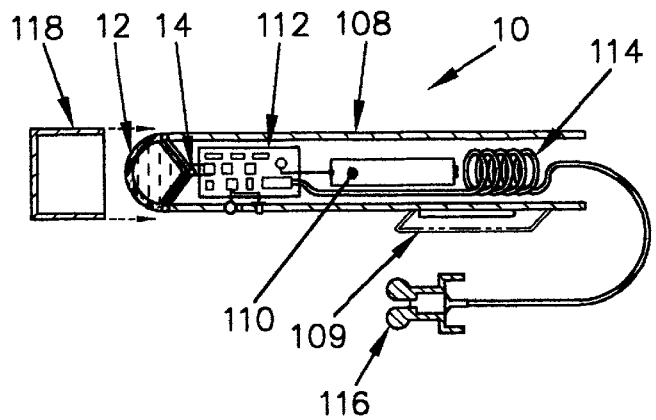
FIG. 11 is a view in cross-section of a hand-held pocket-clip version of an acoustic monitoring system according to the present invention.

A hand-held embodiment of the acoustic monitoring system according to the present invention, shown in FIG. 11 at 10, is configured as a pocket clip sensor and includes a miniature hydrophone or similar transducer 14 mounted within a fluid-filled sensor pad, bladder or diaphragm 12 affixed to a first end of a fountain pen sized carrying case 108 with a pocket-clip 109. A battery 110 powers a processing electronic amplifier and filter package 112, and an internally storable coiled cable 114 carries the sensed signals to an ear-piece 116 for medical monitoring. If an additional ear-piece is provided, biaural, binaural and stereo monitoring can be performed in addition to monaural monitoring. In use, the pad 12 at the tip of the pen case is placed in contact with the clothing or skin of the patient and acoustic information received by the transducer is processed and monitored using the ear-piece. A protective cap 118 fits telescopically over the tip of the pen case to guard against bladder puncture between uses.

Figure 12:
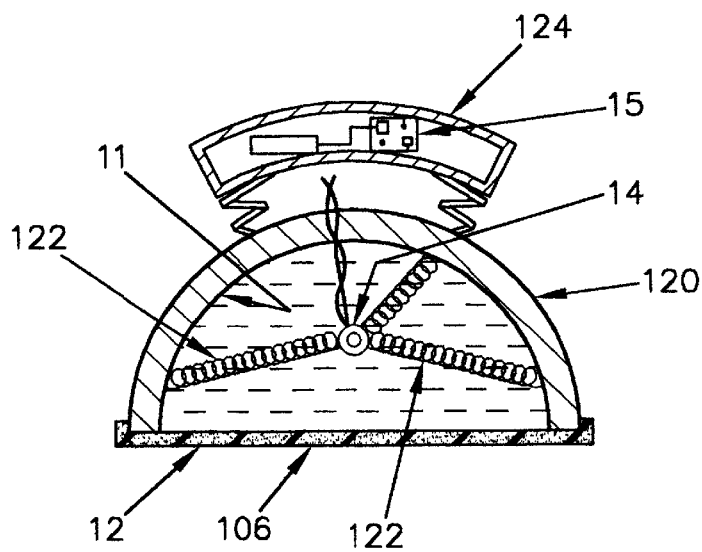
FIG. 12 is a cross-section of a hand-held hemispheric acoustic monitoring system according to the present invention.
Figure 13:
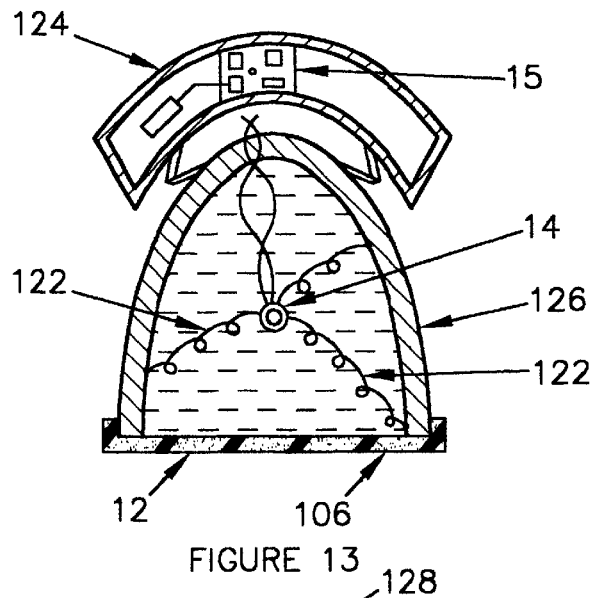
FIG. 13 is a cross-section of a hand-held parabolic acoustic monitoring system according to the present invention.

An alternative embodiment of a hand-held acoustic monitoring system according to the present invention, shown in FIGS. 12 and 13, includes a concave fluid-filled vessel or dome 120 made of or coated with an anechoic, attenuating, non-acoustic material to minimize unwanted airborne and handling noise, and enclosed on a flat side by an acoustically transparent, diaphragm or bladder 106 to define a sensor pad 12 with a fluid-filled chamber 11 therein. A hydrophone or other transducer 14 is mounted within the dome by a vibration isolation suspension system of, for instance, springs 122, and is preferably located at or near the dome focal point to maximize signal reception. An acoustically isolated gripping handle 124 contains necessary power, processing, and transmitting components 15. A hemispherical dome 120 is shown in FIG. 12, but other shapes and configurations can be used including, but not limited to, the parabolic reflector dome 126 shown in FIG. 13 which is particularly useful for focusing plane waves to a point. The hand-held monitors shown in FIGS. 12 and 13 can, for example, be used like conventional stethoscopes by grasping handle 124 and placing the diaphragm of pad 12 against the body or skin of a patient. The excellent acoustic coupling to the monitoring pad does not depend on cleanliness or placement on the pad, thus reducing time required to establish vital sign linkages. Furthermore, a bloody or muddy body placed on the sensor pad might actually couple better to the sensor through the wet clothing than would occur through dry clothing.

Figure 14:
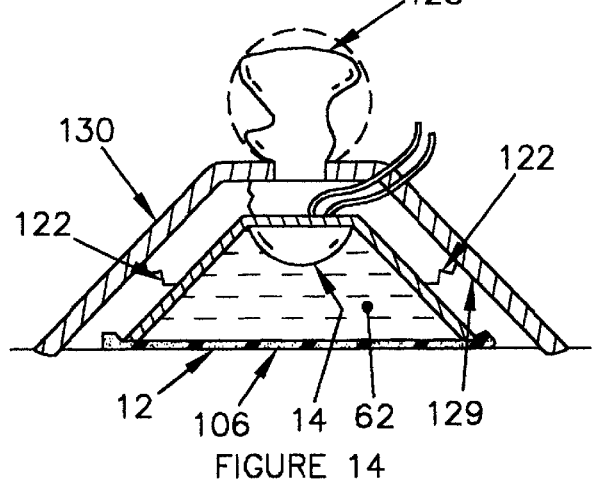
FIG. 14 is a cross-section of a vacuum-attaching embodiment of an acoustic monitoring system according to the present invention.

A vacuum suction attachment for an acoustic monitoring system according to the present invention is shown in FIG. 14 and includes a frustoconical or bell-shaped housing 130 disposed around a sensor pad 12 with a gap or space 129 defined therebetween. A squeezable ball 128 disposed at the top of the housing is communicated with the space 129 to evacuate the air in the space between the pad and the housing prior to attachment to the skin. When squeezing pressure is removed from the ball after the housing seals with the skin, the expansion of the ball, due to mechanical properties of the ball material or spring mechanisms, creates a negative pressure within the gap or space 129 drawing the skin in a little, and maintains a suction force until the seal is broken intentionally. The force of the suction firmly presses pad 12 against the skin to be monitored, and the transducer 14, suspended in fluid 62, receives the incident pressure variations for subsequent processing and output.

Figure 15:
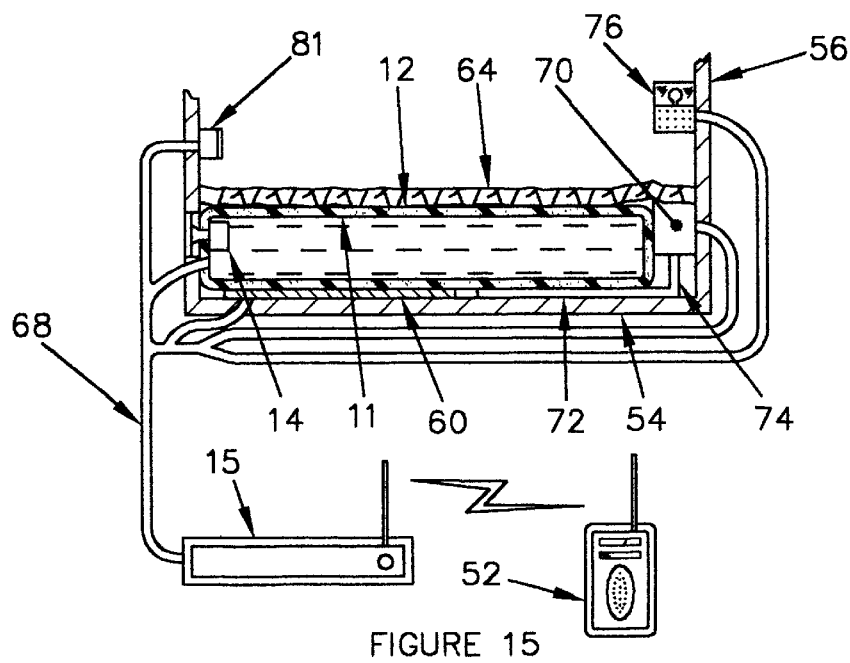
FIG. 15 is an illustration, partly in section and partly schematic, of a baby crib equipped with an acoustic monitoring system according to the present invention.

In higher noise environments, such as helicopter and ambulance transports, it is very difficult to monitor heartbeat, breathing, and voice, due to the very high acoustical ambient noise. Techniques for removing the ambient sounds, such as adaptive filtering, noise reference microphones, acceleration sensors, baffles and other passive means such as sound absorbent materials, can be readily applied to sensor pads of the present invention. For example, in FIG. 15, a modification of the acoustic monitoring system is shown wherein the sensor pad 12 is disposed on a bottom support 54 of a bassinet or crib 56 and an air-mounted microphone 81 is attached to a side rail or the like externally of the pad. Output signals from the transducer 14 within the pad and the air-mounted microphone 81 can be monitored on-site or transmitted via cable 68 to a signal processor 15, for example to be transmitted to a remote receiver 52. By comparing the sounds transduced with the airborne and pad sensors, adaptive noise reduction techniques can be used to remove airborne sounds that couple with the sensor pad. The measured signal level can be monitored aurally and/or compared to preselected stored data to indicate a condition requiring intervention in the form of a stimulation signal or an alarm. If intervention is required, processor 15 can be adapted to actuate vibratory stimulating means 70 connected to pad 12 in order to shake or otherwise move the pad or disturb the baby disposed within the crib and/or to actuate audio/visual stimulating means 76 attached to a side rail of the crib or otherwise disposed to assure stimulation of the baby. Suitable processor circuitry is described in applicant's copending patent applications Ser. No. 08/231,081 now U.S. Pat. No. 5,515,865 and Ser. No. 08/292,441, now abandoned, the disclosures of which were previously incorporated herein by reference. In one embodiment, for example, a voltage comparator constantly monitors the output signal from pressure transducer 14 (or the signal resulting from adaptive noise reduction) and provides acoustic signal comparisons with predetermined stored patterns. If the signal falls below a preselected threshold level or produces a pattern outside a predetermined range of acceptable values, appropriate timing and alarm circuits activate the visual and/or audible alarm. The control circuitry can also be used to apply a reactive or corrective stimulus to the pad 12 via solenoid 70 adapted to shake a rigid member 72 through a solenoid plunger 74 to create physical shaking of the pad so as to physically stimulate the monitored baby. After the stimulus has been applied for a predetermined length of time, as determined by the timing circuit, the circuit may reset to the normal monitoring condition to evaluate whether the stimulus was effective. If not effective, the stimulus may be reapplied and the alert sounded or resounded. With the use of the transmitter, the responsive signal being generated can also be monitored.

Another unique feature of the invention which may be achieved through the vibrating means or shaker means connected to the pad 12 and operated by the processing means 15, is the ability to operate the shaker in a quieter, soothing amplitude mode to promote relaxation. Appropriate circuitry modifications to the detection circuitry will be obvious to one of ordinary skill based upon this disclosure.

Sudden Infant Death Syndrome (SIDS) and apnea monitoring can use such a fluid-filled sensor pad, on which the baby lies, to gather acoustic data. If acoustic signature analysis of the output indicates a cessation of breathing or heartbeats the device stimulates the child with sound, light, vibration, or other methods while simultaneously alerting the attendants via transmitter or alarm that immediate response or resuscitation is necessary. Using time-frequency analysis, amplitude relations, or temporal cues, cries of baby can be useful for determining mental state, health, pain, suffering, uncomfortableness, drug effectiveness, etc. Lights and a speaker provide continuous awareness of the infant's well being by presenting sounds of breathing, heartbeats, vocalizations, and other bodily noises. Even if the baby were sleeping quietly in a very quiet room, the monitor would indicate heartbeats and breaths, whereas standard baby monitors would not give any indication of child's health or whether the monitor was picking up anything at all. In a noisy environment, such as a TV viewing room, parents monitoring their child with the present invention may find it more useful to place the remote monitoring component of the present invention in their field of view and not necessarily listen to the remote speaker's presentation of the heartbeats and breaths, but rather view blinking lights representing the child's well being (such as the occurrences of heartbeats and breaths, or an additional light that may indicate crying).

Figure 16:
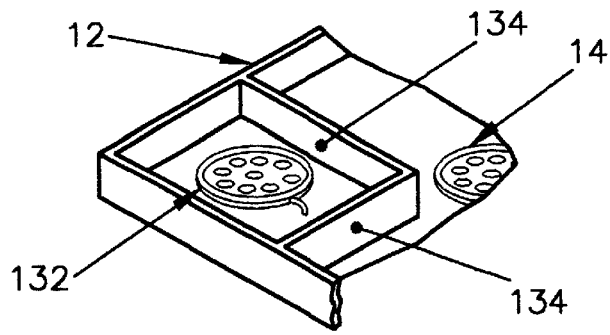
FIG. 16 is a partial perspective view of a fluid-mounted reference sensor shown in cutaway.

A reference microphone or transducer can be placed at any suitable location depending upon the specific application. For example, a reference transducer could be located inside the sensor pad within the liquid or fluid at an acoustically isolated location from the monitored organism, so that this reference transducer would pick up only airborne sounds coupling to the pad, but not sounds coupling from the organism on the pad. One such reference transducer, shown in FIG. 16 at 132, is acoustically isolated from the chamber containing the primary or sensing transducer 14, by for instance walls 134, but is otherwise exposed to ambient environmental input. The wall thickness of the pad 12 and any other receiving surface disposed between the pad and the organism is preferably uniform over both the primary and reference sensor to ensure similar coupling impedance. Therefore, the difference (or transfer function) between the reference section output and the main sensor pad output would be the patient's contribution, free of the ambient noise.

Bandpass filtering can separate heartbeats, breaths, vocalizations, and motion. For example, the circuitry could high pass the transducer output signals above 350 Hz or so for cries, sniffles, voice, etc. An alternative embodiment of the monitor could have a filter that only allows high passed vocalizations to be presented by a speaker, and only displays on light indicators the low-frequency information indicating the occurrences of heartbeats and breaths. An alarm mechanism could be implemented to analyze the hydrophone output to detect and react to certain conditions, such as crying, absence of heartbeat or breaths, or any other acoustically definable characteristic, such as coughing, snoring, or sneezing.

Figure 17:
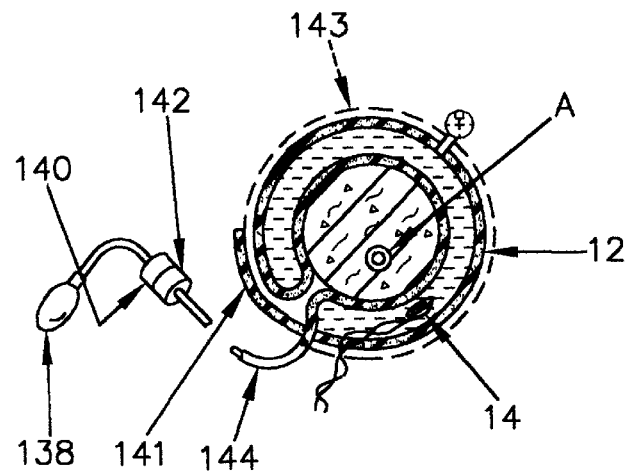
FIG. 17 is a cross-section of a single compartment acoustic monitor blood pressure cuff according to the present invention.

The acoustic monitoring system, can be embodied in a blood pressure cuff, as shown in FIG. 17, by adapting sensor pad 12 to have a cuff-like configuration and mounting one or more transducers 14 therein with at least one of the transducers preferably oriented adjacent the artery A. The pad is preferably constructed of rubber and can be optionally covered by a thin structural cloth or mesh material (shown by broken lines at 143) to maintain cuff shape yet allow efficient transfer of pressure signals from the arm or torso of a patient into the liquid-sensor chamber. If desired, the cover material can be acoustic insulation to limit air-coupled noises. A pressure bulb 138 is used to apply pressure to a bladder-piston assembly 140, pressurizing a liquid reservoir 142, hose 144 and the sensor pad or cuff 12. At least a portion of the outer surface of the arm-encircling pad or cuff bladder can be pressed simultaneously against the torso to acquire additional heart and lung acoustic and timing data. Alternatively the cuff outer surface can be acoustically insulated to minimize the incursion of ambient noise. The use of a plurality of transducers in the same cuff, arranged around the perimeter of the arm of the patient could maximize the system sensitivity to sound originating near the center of the arm, each having approximately equal time delays to add in phase. Use of two transducers would also allow binaural auscultation.

Figure 18:
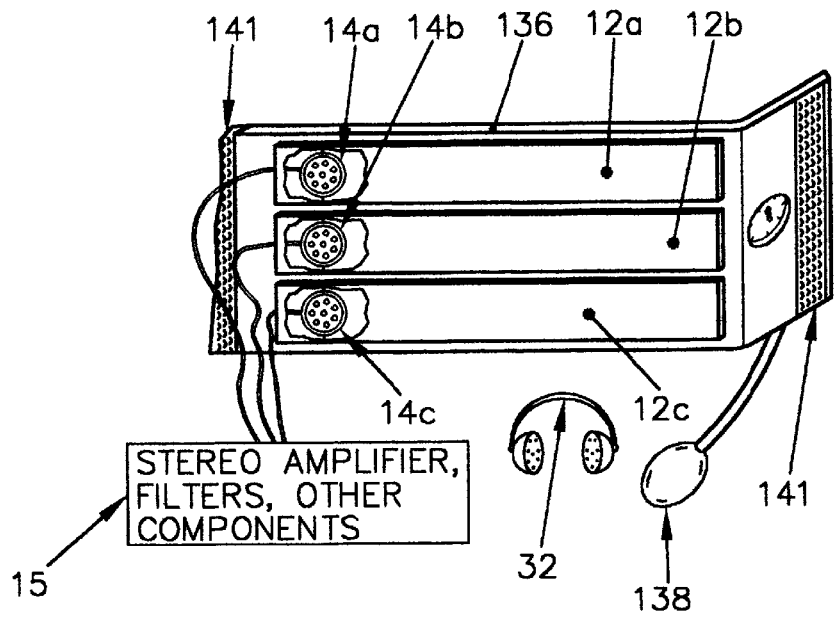
FIG. 18 is a perspective view in partial cutaway of a multi-pad acoustic monitor cuff configured as a blood-flow/blood pressure monitor.

As mentioned previously, the sensor pad could contain one or more compartments or pad sections, or multiple sensor pads can be mounted on a single support or backing material when plural output signals are necessary or desired. In FIG. 18, for example, a blood pressure cuff 136 is shown having three elongate fluid-filled bladders or pads, 12a, 12b and 12c, each provided with separate acoustic transducers, 14a, 14b and 14c, respectively, disposed therein. The blood pressure cuff 136 is configured to encircle a limb, with self-attaching connector material 141 such as VELCRO, and a pressurization bulb 138. A headset 32 allows binaural or multi-channel monitoring of the acoustic signals. Obviously the monitored signals could be processed individually, or combined in various ways to perform spatial and temporal filters, beam formers, noise cancellation beam formers, and other signature extraction techniques as applied in array theory. Omni-directional or directional acoustic sensors can be employed to aid in sound reception. Mechanical focusing and impedance matching mechanisms, such as reflectors, lenses, baffles, or horns can provide directional sound reception sensitivity, gain, and filtering. A grid array could be configured in order to pick up sounds emanating from different areas of the body, such as throat, upper aorta, left versus right ventricles, lungs, intestines, etc. The system could also be configured as a torso cuff to artificially stress the heart and lungs for health evaluations, including treadmill stress testing for cardiovascular assessment.

Figure 19:
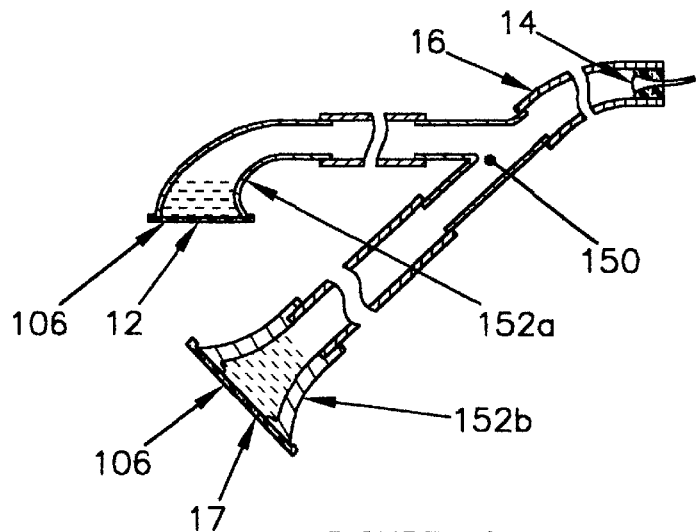
FIG. 19 is a broken cross-section of a folded exponential horn and an exponential horn embodiment of the present invention each in fluid communication with a single transducer.

Pads with multiple chambers and acoustically isolated transducers were previously shown in FIG. 3. Alternatively, multiple chambers can feed simultaneously or switchably into a single transducer 14 arranged in continuous fluid communication with each of the chambers as illustrated in FIG. 19, where a junction 150 unites the output of two or more similar or variously configured sensor pads 12 shown, for purposes of illustration, as a pair of diaphragm-covered exponential horns 152a and 152b.

From the above, it will be appreciated that the present invention can be used to monitor the peripheral pulses in the extremities with a monitoring band attachment that can be placed around the wrist, arm, leg, neck, forehead, ankle, torso, or abdomen. A cylindrical or tubular, continuous or compartmentalized, pad configuration with one or more transducers can be wrapped around various body parts to acoustically couple to the body at specific locations or continuously over an area. Radial artery pulse measurements from a strip sensor in the form of an acoustic monitoring band can analyze blood flow in limbs, heart, head, neck, etc. Modifications to the device may allow blood pressure and flow measurements to be determined from the acoustic signature sensed when a condition of blood flow constriction is induced. This constriction of flow could be from a tourniquet device such as a blood pressure cuff, or by a pressure inducing force. A standard blood pressure cuff could be modified to use a water-filled bladder with a hydrophone that is pressed against the skin when an air bladder in contact with the liquid medium is pressurized with a pressure bulb.

The placement of the hydrophone should preferably be close to the artery to monitor the changing acoustic signature of the flowing blood as the artery is constricted with increasing pressure from the cuff, and to monitor the acoustic signature as the pressure is released and blood begins to flow through the constricted artery. For medical research applications, restricting the flow of blood to the torso, abdomen, neck, extremities, or head could have physiological effects indicative of heart, lung, or vascular performance. Acoustic analysis may indicate strength of heart, condition of artery walls, dimensions of passageways, flow noises at specific locations, volume of blood flow, and flood pressure, and may help with diagnosis.

Positioning of the hydrophone within the cuff can also permit coupling with the torso if the cuffed arm is held in tight contact with the side of the torso. By detecting and isolating both the heart sound and the resulting radial extremity signal, significant information may be inferred as to the health of the heart, time it took to travel from the heart to the arm, modification to the acoustic signature, etc. For civilian telemedical applications, this will also make overall health assessments easier, since positioning of the sensor would be relatively constant, and the sensor would not need to be readjusted for blood pressure and cardiovascular evaluations.

Figure 20:
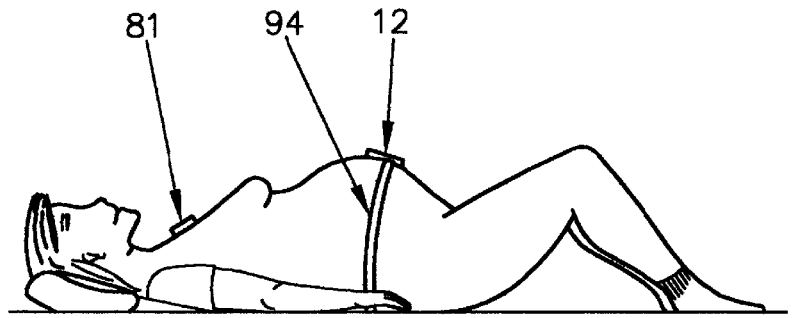
FIG. 20 is a side view of an acoustic monitoring system according to the present invention applied to a pregnant woman to monitor fetal heartbeat activity.

The excellent sensitivity of the present invention and efficient coupling to the human body can enhance fetal heart monitoring, as shown in FIG. 20, by placing the sensor pad 12 adjacent the mother's womb, for example using a strap or belt 94 that wraps around the mother's waist. Fetal health can also be assessed by heart-rate and by the amount of fetus movement, which could be detected acoustically with the present invention. Fetal breath and motion sounds may be in the infrasonic frequency range, and therefore not perceived in normal auscultation with a stethoscope. A reference microphone 81 and signal processing techniques can be used in the manner previously described to remove the mother's heartbeat and breath sounds.

There is also the potential to apply mechanisms (mechanical, electrical, chemical, etc.) to stop or prevent continuation of any physiological condition that has been detected acoustically, such as the onset of heart attack, stroke, arrhythmia, respiratory distress syndrome, heart rate variability, intestinal distress, gas, onset of bowel movement or urination. The present invention technology could replace current home spirometry devices that monitor volume flow of lungs to determine rejection/acceptance of lung transplants or could help verify artificial heart or heart valve replacement performance, either at the location of the patient, or telemedically via telephone or radio links.

When combined with EEG/EKG/ECG/EMG etc, the present invention can collect correlative data that relates sounds of body functions to that of electrical signals of the body. For example, the electrocorticogram (ECG) uses subdural electrodes on the cortical surface to detect and localize epileptic seizures. Electrical monitoring on the cortical surface will indicate increases in frequency of harmonically related chirps prior to onset of full seizure. If the present invention could detect acoustically related components associated with these electrical impulses, such as muscle spasms/ activity, cardiopulmonary activity, or other torso/ gastrointestinal sounds, non-invasive home monitoring could be used to detect the onset of seizures. This may be extremely valuable to epileptics that drive vehicles, or who's work environment could jeopardize themselves or others in the event of seizure. Monitoring of cardiovascular signals and early detection of body convulsions or particular patterns in muscular/skeletal motion could lead to early intervention for seizures and other medical or psychological conditions, such as depression. The brain also creates electrical signals associated with mental activity, for example a 10 Hz alpha band rhythm in reaction to planning of movements. There may also be acoustic signatures that could be monitored simultaneously using the sysem of the present invention, that would correlate to these electrical impulses.

Because the transducer can be placed some distance away from the center of the acoustic target area, either in the chamber 11 or a fluid-filled conduit or channel communicated with the chamber, the sensor pad can be made essentially non-metallic and non-electronic for use in the field of view of X-ray, CT scanner, MRI, and ultrasound imaging systems. During MRI, the magnetic resonance may induce some acoustic signals that may be detected by the pad acoustically. Nuclear magnetic resonance looks at hydrogen for imaging (randomly oriented in absence of magnetic field, aligned in magnetic field). Magnetic field modulation could produce tissue resonances that could be monitored acoustically. These monitored acoustic body resonances/responses resulting from the application of forces or stimuli, such as acoustic, magnetic, electric, or other forces (mechanical, electrical, chemical, biological) could indicate tissue, bone, or skeletal condition or type when acoustic signature analysis is applied. The passive nature of the present invention would provide continuous and immediate heartbeat and breath data, but would not interfere with ventilators, defibrillators, or other surgical equipment used in the operating room.

The acoustic monitoring system could be incorporated in or attached to an implanted prosthetic device or artificial heart, with an RF or inductive link to relay the acoustic information outside the body, if desired.

Figure 21:
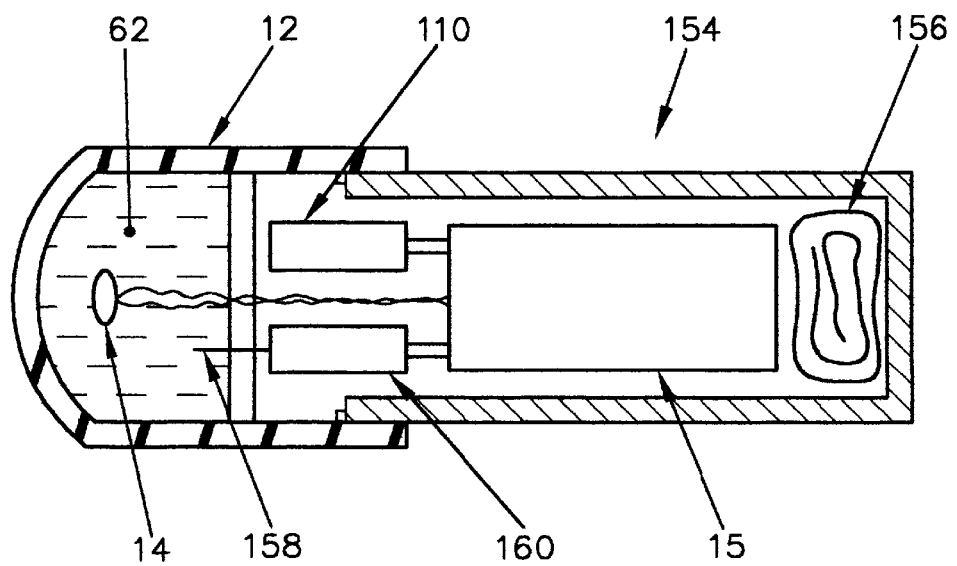
FIG. 21 is a cross-section view of a swallowable capsule configured with an acoustic monitoring system according to the present invention.

The acoustic monitoring system can be implanted or inserted into the body of a living organism, or swallowed in the case of humans and animals, to provide better coupling and ambient noise reduction. For example, in FIG. 21, a capsule 154 is shown having a sensor pad 12 with a transducer 14 disposed therein at one end of the capsule body, and processor components 15, such as an amplifier, filter and encoder, transmitter and an antenna 156, at the other end of the capsule body, the body being formed of a material able to withstand the harsh environment of the human stomach while still allowing coupling to internal walls of the stomach or intestines. A temperature probe 158 and conditioner 160 are also provided. There may, however, not be a need to have a battery enclosed, since inductive and RF techniques are available to transmit small amounts of power to circuitry within the body, thereby reducing the size and cost of the implanted device.

Figure 22:
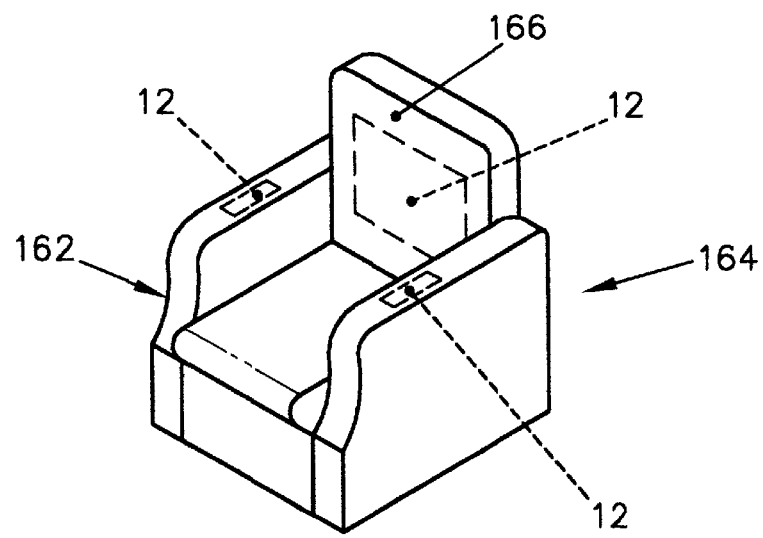
FIG. 22 is a perspective view of an arm chair having an acoustic monitoring system according to the present invention installed in the chair back and arm rests.
Figure 23:
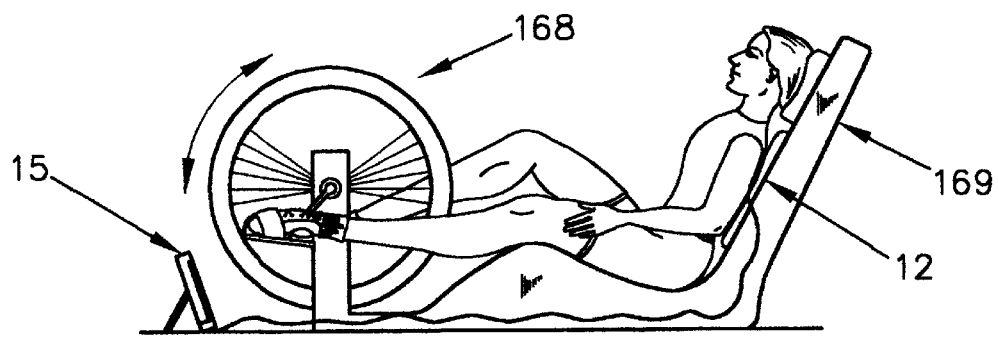
FIG. 23 is a side view of an acoustic monitoring system according to the present invention installed in the back and head rest of a recumbent exercise bicycle.

A sensor pad can detect heartbeat and breath information when attached to or built into a baby seat, chair, seat, back cushion or other support surface of a wheel chair, geriatric chair, or exercise machine, such as a recumbent or reclined bike. This information can be useful for determining the health state of the person or animal in contact with the sensor or as a covert sensor for lie detector applications, voice print recognition, biofeedback or stress management. As shown in FIG. 22, a pad 12 mounted on the armrest 162 of a chair 164 can detect radial pulse and a thin leather-like material of the chair back 166 with acceptable acoustic transfer function could cover or serve as the outer surface of a fluid-filled bladder or pad 12 with a hydrophone or transducer within, and could also incorporate a temperature probe to detect heart, breath, and vocalization sounds. Signal conditioning and processing could be accomplished by a battery pack, filter, transmitter, tape recorder, or other support electronics contained inside the chair or cushions. An ambient air microphone can be incorporated into the acoustic monitor system to calculate the transfer function between the airborne spoken voice and the voice coupling to the fluid-filled back cushion through the person's body. This transfer function would be a form of identification similar to a voice-print and can also be used as a voice-stress analysis data source. For home or office stress or biorhythm feedback, a headset (audio) output can be combined with a visual display of measured parameters, such as heart and breath rates or blood pressure. The use of a sensor pad 12 according to the present invention is shown in FIG. 23 applied to a support surface of exercise apparatus and equipment, in this case to the back support 169 of a recumbent bicycle 168, to monitor aerobic output. A SIDS or apnea monitor using the acoustic monitoring system according to the present invention would be useful while transporting children in cars or car-seats. Sensors could be incorporated into under-arm crutches pads, prostheses, orthopedic structures or postural aids to acoustically monitor patients. Patients in wheelchairs could travel the halls of a hospital while being monitored, and telemetry mechanisms could alert attendants in the event of circulation or respiratory problems, or if they leave the wheelchair. For health performance monitoring and for patients recovering from surgery, heart and breath rates could be monitored to limit exercise or maintain minimal levels.

Figure 24:
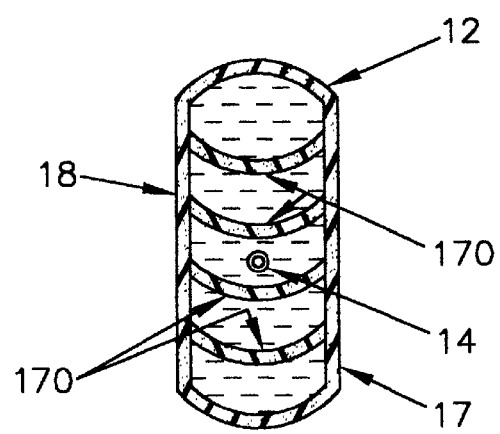
FIG. 24 is a cross-section of an acoustic monitoring system according to the present invention with shape-retaining internal stiffening structure for supporting vertical orientations.

In many applications a vertical orientation is preferred for the fluid-filled pad or bladder, as for instance, when used in the back of an exercise device, a vehicle seat or chair. Flexible yet shape-maintaining interior baffles or supports 170, as shown in FIG. 24, are formed to be acoustically transparent and extend transversely between opposed, vertical walls 17 and 18 of the pad to provide the required structural integrity and to help avoid gravity-induced changes in shape.

Figure 25:
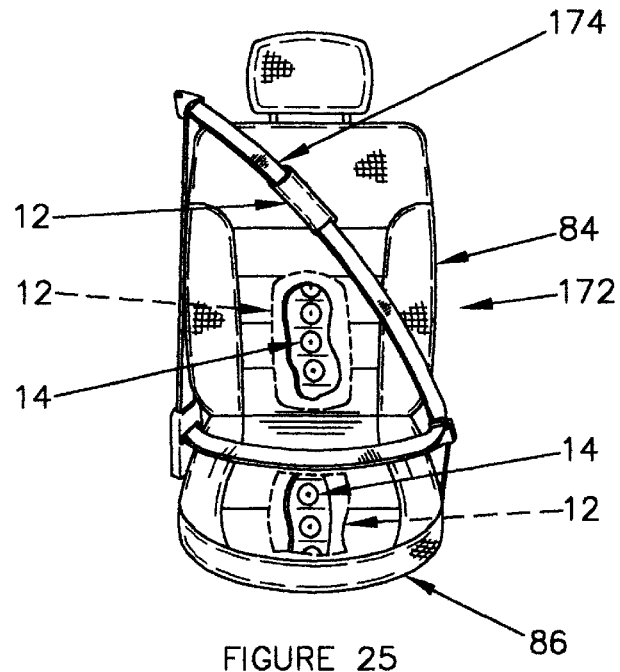
FIG. 25 is a perspective view in partial cutaway of an acoustic monitoring system built into a vehicle seat back and seat belt for monitoring driver alertness.
Figure 26:
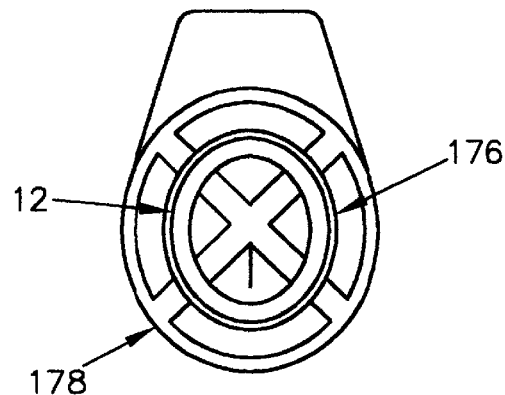
FIG. 26 is a top view of the interior of a hat or cap configured with an acoustic monitoring system according to the present invention attached to the hatband.
Figure 27:
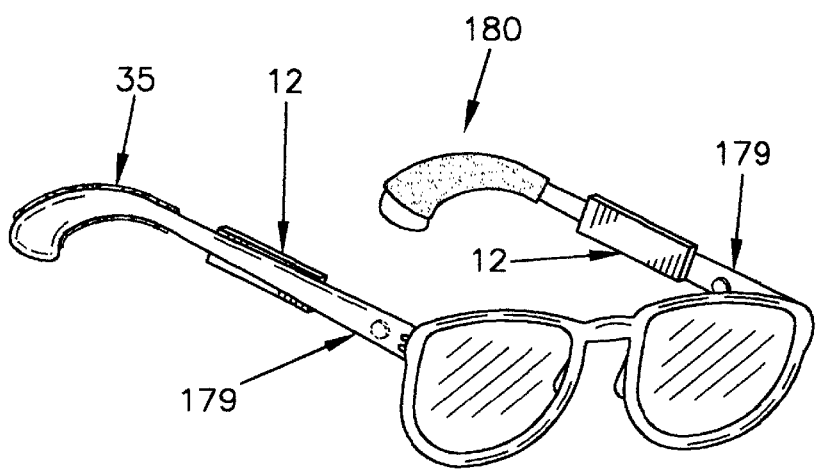
FIG. 27 is a perspective view of an acoustic monitoring system according to the present invention attached to eyeglasses.
Figure 28:
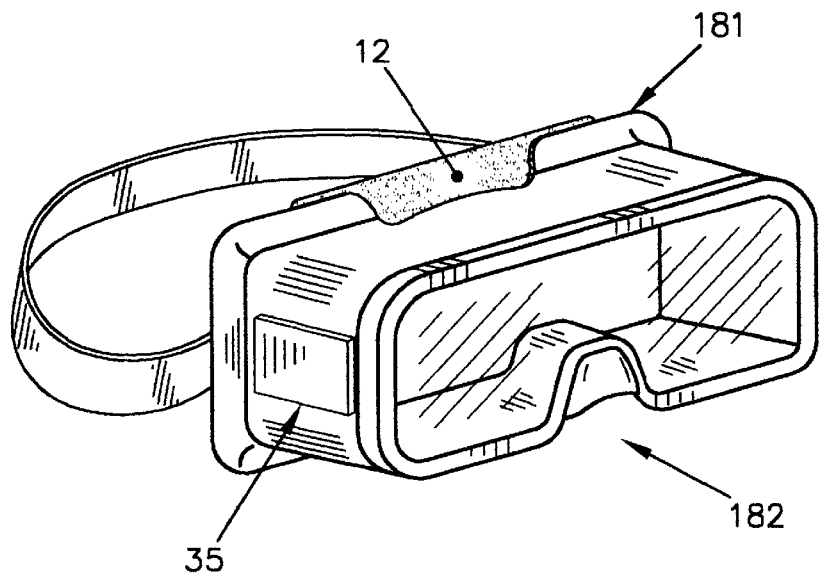
FIG. 28 is a perspective view of an acoustic monitoring system according to the present invention attached to a pair of goggles.
Figure 29:
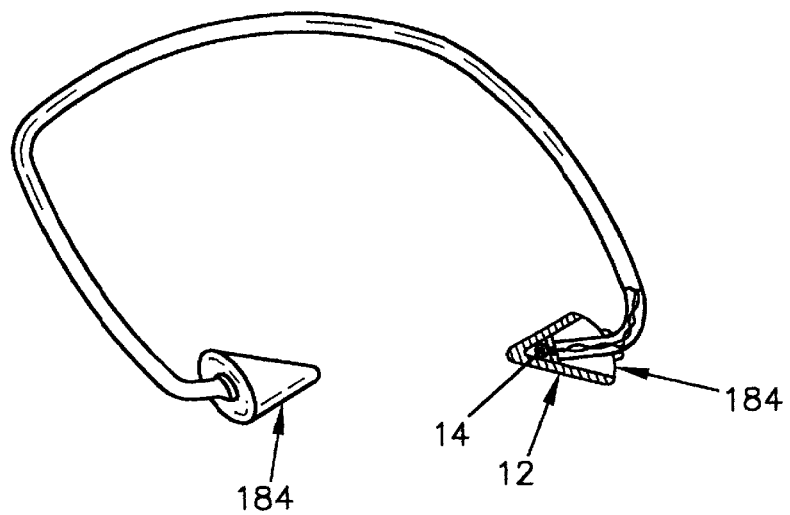
FIG. 29 is a perspective view in partial cutaway of an acoustic monitoring system according to the present invention built into ear plugs.

When built into transport seats or as an attachment to the seat or safety belt as shown in FIG. 25, the technology can also be used to monitor or to alert vehicle or machinery operators that the pad has detected the onset of sleep, which may be characterized by a marked decrease in heart and respiratory rates, or changes in heart-rate-variability. One or more acoustic sensor pads 12 and stimulators can be built directly into the seat cushion 86 or back 84 of a vehicle seat 172 or held against the torso of the driver by the vehicle seat or chest belt 174. Since every person's metabolic rate is different, the pad could use an autocalibration technique to set detection parameters based on when the person has been sitting down in the seat for a short period of time. Medical experimentation could define the percentage of decrease in cardiovascular rate necessary to be indicative of sleep or semiconscious behavior. A sensor pad 12 and, optionally, a stimulator 35, can be miniaturized and built into the headband 176 of a cap or hat 178 as shown in FIG. 26, included in the arms 179 of glasses 180 as shown in FIG. 27, attached to support surfaces 181 of safety, scuba, aviation, firefighting or other types of protective goggles 182 as shown in FIG. 28, or included in insertable ear plugs 184 as shown in FIG. 29. The acoustic monitoring system of the present invention can also be combined with other forms of sleep detectors, such as head tilt sensors, or eye closure sensors. Once the technology has detected the possibility of sleep onset, stimulation mechanisms (e.g., elements 35 in FIGS. 27 and 28) can be implemented to alert or wake car drivers, train conductors, pilots, tankers, truck drivers, and operators of equipment. Stimulation can be in the form of alarm, vibration, ventilation, increasing radio volume, or temperature adjustment, for example. Appropriate filtering and noise cancellation techniques can be implemented to remove or reduce vehicle noise and vibrations, and other transducers or sensors can be combined to enhance signature collection or noise reduction, such as accelerometers, motion and displacement sensors, or other technologies.

The technology of the present invention can be used as a heartbeat detector for a "deadman" or safety switch, to either prevent a piece of machinery (such as, for example, a forklift or train) from operating unless there is a heartbeat, or to initiate corrective measures in the event that a heartbeat stops. For instance, control of an aircraft can be shifted into "auto pilot" when the pilot is either shot in a battle situation or has a heart attack, seizure, or leaves the pilot seat for any reason. Additionally, in micro gravity and hyper gravity environments, changes in heart rate can be related to oxygen demand, so the present invention can be used to detect fainting or pilot black-out. As an added safety feature, the heart rate detector could automatically apply an emergency brake or ignition cut-off, for example when no heartbeat was detected, and prevent accidental movement or engagement of heavy or dangerous equipment in the absence of a predetermined operator acoustic signal.

Home and office monitoring of heartbeat and breath information can give feedback directly to the person sitting in a chair or bed for purposes of biorhythms, stress management, hypnosis, or performance optimization.

Figure 30:
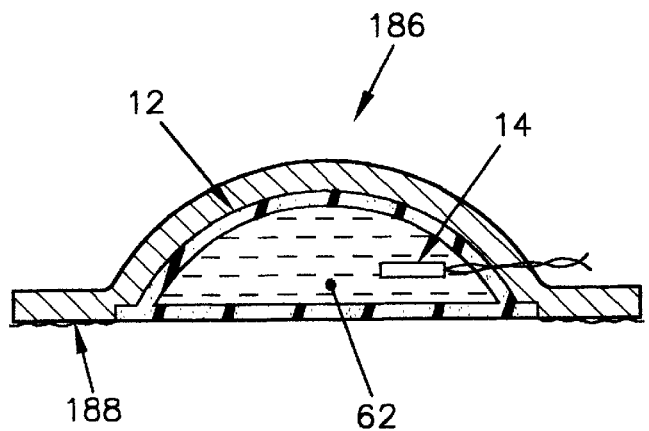
FIG. 30 is a cross-section of an adhesive-mounted acoustic monitoring system.

Unlike traditional throat microphones, a tube-like choker with a transducer according to the present invention can detect voice, heartbeat, and breath sounds from peripheral neck-region contact, in addition to throat and ambient noises. A small pad 12 can be incorporated into a patch 186 held by adhesive 188 to the skin as shown in FIG. 30, or attached to the collar or dog-tags, to monitor heartbeats, breaths, and voice. An acoustic monitoring system according to the present invention can also be built into load-bearing gear, bullet-proof vests, shirts, vests, jackets, bras, or other garments or configurations to be held next to the body for law enforcement agents, security personnel, firefighters, scuba divers, soldiers, and disaster relief personnel in hazardous situations. Personnel equipped with small monitoring sensor pads in contact with their torso could be medically interrogated from a remote location, and remain passive (monitor without transmission) otherwise, to conserve power and prevent disclosure of location by RF emission. Data can also be transmitted by IR, ultrasonic, induction, laser, and other technologies.

Squad or team performance levels could be assessed or those missing in action could be medically interrogated from a remote location. The addition of a temperature probe, GPS, time, and personal ID tag (by various frequencies, AM/FM modulation, PCM, or digital technologies) would improve monitoring effectiveness and allow recovery if necessary. Pager tagging methods could select which person was to be interrogated, and alert him to pause for data collection, or respond by transmitter in such a way when pinged, indicating whether medical rescue is necessary, or other medical situations exist which may need attention.

An acoustic monitoring system with a stimulation mechanism according to the present invention can be incorporated into pillows or head supports to be used to detect and stop snoring, talking in one's sleep, sleep walking, SIDS or sleep apnea. Many forms of sleep obstructed apnea syndrome could easily be detected and interrupted by monitoring breathing with an acoustic pad of the present invention, either incorporated into pillow or in contact with torso. Once a sleep walker sits up in bed or leaves the bed, heart rate and breathing information will be lost, and an alarm can wake the sleepwalker or companion.

When the acoustic monitoring system is used as a stethoscope, the hydrophone coupling to the body through the fluid-filled sensor pad eliminates the body-air interface losses that result when a standard stethoscope's bell is in contact with the skin. Additionally, the hydrophone's fluid coupling to the body eliminates the various acoustic impedance mismatches and sound transmission effects within the stethoscope's tube as the sounds travel to the ears. Implementational advantages of the sensor pad over standard esophageal and precordial stethoscopes include non-invasive monitoring and enhanced acoustic coupling for acoustic signal collection and transmission. The transducer in the fluid-filled system would preferably be a piezoelectric, electret, or condenser-based hydrophone, similar to those used by the Navy in sonar applications. Other water-proof pressure and motion sensing technologies could also be applied.

Figure 31:
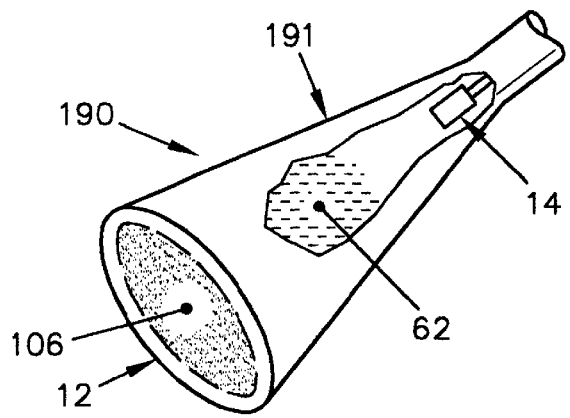
FIG. 31 is a view in cross-section of a stethoscope according to the present invention.

A doctor might use such a device in place of a standard stethoscope as shown in FIG. 31 at 190. Enhanced listening can be achieved through improved coupling and by reducing the impedance mismatches and acoustical losses and resonances due to the air filled stethoscope bell and tube. There are electronic stethoscopes available that utilize an airborne microphone positioned at the apex of the standard stethoscopic bell. This has significant acoustic impedance mismatches and resonances associated with it. A liquid-mounted hydrophone 14 could replace the air microphone, a thin polychloroprene rubber diaphragm 106 could replace the plastic diaphragm and cooperate with the rigid bell portion 191 to define a sensor pad 12 filled with liquid 62 to improve acoustic coupling and eliminate losses from the transfer of liquid borne sound to airborne pressure fluctuations. Other modifications can be made for oral, anal, vaginal, esophageal, and external monitoring devices. This technology can be applied for better acquisition of fetal cardiac sounds, either through vaginal probe or externally on the mother's stomach as described above.

Veterinarians and other professions may also use a smaller hand-held acoustic monitoring device, either held in contact with or strapped to the animal, or if manufactured small enough, ingested, for purposes or medical health or endurance level monitoring of race horses, dogs, other animals, or humans. A small version of the present invention could be configured as a wrist support or trackball support for detecting heart rate for games, health-monitoring, stress reduction, identification, and interactive computer diagnostics.

Depending on the application, a surgical irrigation tube or intravenous supply could be used as a fluid-filled extension and connected to a transducer. Just as light travels through a fiber optic, sounds would travel through the fluid-filled tube with minimal losses. This tube can lead to a transducer that is coupled to the tube itself, or to the liquid reservoir, such as an IV bag. One configuration of the present invention can clip onto the tube or to the bag and pick up heart sounds, especially when the tube picks up venous pulsations. The present invention could be used to vary the flow rate of the IV if necessary. For example, if heart rate was a good indicator of pain or sleep state, medication could be varied in response to rate.

Information collected with any configuration of the technology of the present invention could be monitored on the spot or transmitted by radio to more qualified medical personnel for remote diagnostics. Doctors could do a complete health assessment remotely while a patient is lying with their back or stomach in contact with the pad. Paramedics, nurses, emergency medical technicians, and medics can carry such a pad to monitor "hands-free" and transmit the data over standard radio links to more qualified medical personnel for remote diagnostics.

Figure 32:
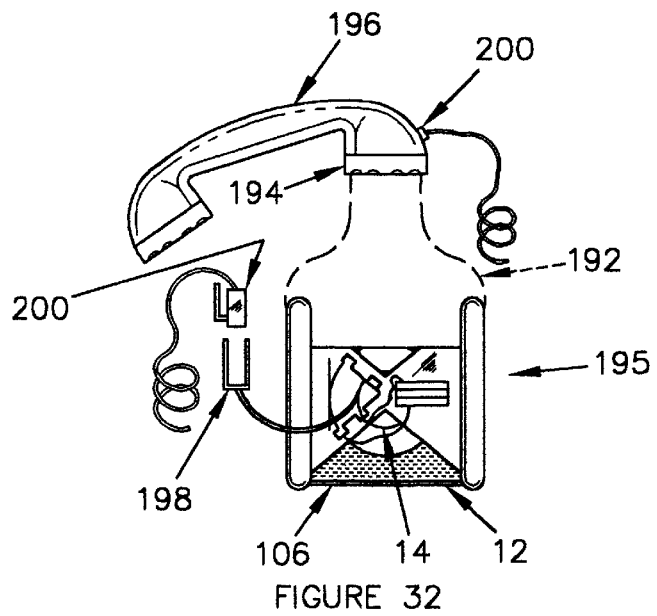
FIG. 32 is a broken cross-section of an acoustic monitoring system according to the present invention configured to transmit sensed signals over telephone lines.

Other implementations of the acoustic monitoring system technology could include an external microphone for cameras, intercoms, telephones, radios, voice commands for industrial workstations, computers, etc., and other nonairborne noise coupling applications. One such device, a telephone coupler for telemedicine and home check-up is illustrated in FIG. 32 at 195. A flexible cup 192 fits sealingly over the mouthpiece 194 of a standard telephone 196 acoustically coupling an audio output of the acoustic monitoring system to the telephone. Alternatively an output jack 198 can be used to electrically couple the monitoring system directly into the telephone wire jack 200. Health counseling with families, patients, and children can be made easier when the output of the device is broadcast to everyone at the same time through a speaker, public address (PA), or headsets, or visual presentation methods, such as time versus voltage waveforms or spectrograms. Discussions and observations, including diagnosis, can be improved, especially for educational facilities that can broadcast to the entire classroom or operating room.

When built into a blood pressure cuff, where the underarm coupling to the torso would provide the acoustic path to either the torso or to the brachial artery, the present invention can be used at nursing homes, home health care centers, or walk-in health clinics to provide remote audio and video check-up facilities. If a medical monitoring sensor were placed on or underneath a person, the patient could talk during data collection to give symptoms, feelings, and if two way communications were incorporated, the patient could hold their breath when asked to do so by the doctor for better heartbeat information.

Since voice, breath, and heart sounds are typically in different frequency bands, signal separation techniques could be used to allow separable transmission of intelligible speech and high quality medical acoustic data simultaneously. Processed data or raw audio data can be transmitted directly over phone lines, or could be videotaped using the present invention as an external microphone for a video camera, allowing check-ups by mail, phone, or radio. Transmission coupling mechanisms can be standard connectors to radios, telephone jacks, or cup-like configurations that form confined volumes or paths leading to various transmission receiver elements.

Each individual's voice is different and can be used as a form of identification ("voice prints" are common forms of ID). Everyone's spoken word (voice), when monitored through their own body using an acoustic sensor pad according to the present invention, would be unique in itself, especially when correlated with the heartbeat and breath sounds through the same body transmission path. Such a capability could obviously be used for security, anti-theft, computer and facility access control, back-up identification, and legal transaction authorization. When configured as an auxiliary microphone to a video camera, IR sensor, or retina scanner, the combination of voice-print, heartbeat, breath, and imagery would be proof of identification.

Depending on the acoustical content of the heartbeats, chest cavity, lungs, and voice content, the pad could be used as a means of identification for a person when their torso contacts the sensor pad. The acoustic monitoring pad could be built into a chair, such as at money machines, secure entrances, or in automobiles or aircraft as an access limiting, anti-theft or anti-hijacking device. A neural net ID would be perfect for a device that looks at the heartbeats' and breaths' acoustic signatures, while simultaneously looking for the person's spoken name or password. Given a random word to repeat when in contact with the present invention, there would be no way an imposter could duplicate the torso resonances and through-the-body transmission effects of the proper person, nor could they duplicate any heartbeat and breath signature information that may also identify the proper person. An ambient reference microphone could be used to compute the through-the-body transfer function of spoken word, where each person's transfer function would be unique. Although transfer functions would be reasonably constant due to body characteristics such as volume of lungs, throat, nasal and sinus cavities, rib cage, and muscle mass, in addition to accent and physiological pronunciation mechanisms, the identification transfer function could be updated periodically, as changes in muscle mass and weight effect certain acoustic characteristics.

Additionally, the device could be built into a seat or chair, for example as shown in FIG. 22, and used surreptitiously for interrogation or identification. A voice stress analyzer could process the output of the acoustic monitoring sensor, to use voice stress levels, heart and breath rate, and body temperature as a passive and covert lie detector or polygraph.

As a means for limiting access to equipment, the frequency content of heartbeat and breath sounds and their respective rates could distinguish between an adult or a child to prevent improper use of devices such as automobiles, hazardous equipment, or computer equipment. A weight sensor could provide corroborating evidence to help distinguish between an adult and child, by assuming that an adult weighs more than a certain limit, for example, over ninety-five pounds.

Day care centers can incorporate technologies of the present invention to not only guard against SIDS and apnea, but also ensure that the child is present and alive. Such a system can be used as an anti-kidnaping device that would sound an alarm as soon as a child was taken from a bassinet, crib, bed or stroller. Appropriate signal processing can be incorporated into a stroller to remove the motion induced signals.

The system can also be used as a passive, non-connecting way of ensuring the presence of a person, and could easily be used in prison cell mattresses for verification during "roll call". Somnabulators (sleep walkers) could be awakened as soon as they leave the bed, or others alerted to their condition. Obviously the pad could be used for all other animals as well, in veterinary research, zoos, pounds, etc.

The sensitivity and coupling of the sensor pad can be used for equipment or engine diagnostics, or other hardware, and would be ideally suited for monitoring fluid flow noises associated with mechanical conduits, pipelines, or human fluid passage-ways, such as arteries or veins. There would be some transmission losses, as the encasing material would not have the same acoustic properties as the liquid or rubber walls of the present invention; however, excellent coupling could still take place. Once a "not normal" acoustic condition, such as a leak or blockage is detected, appropriate action can be taken. When placed on the ground, an acoustic monitoring system according to the present invention could be used to detect vibrational (seismic) and acoustic activity emanating, or could be configured as an acoustical rain gauge, sensing the acoustical amplitude and rate of raindrop impacts. The number of impulses per second per area of the pad can be used to indicate density of rainfall, whereas signal amplitude would be a function of the velocity and volume of the drop.

The circuitry employed in the preferred embodiment of this invention may also include outputs corresponding to heartbeat and breathing rates, as well as a clock for measuring elapsed time since a last warning, number of incidents, time of cessation of movement or acoustic activity, false alarms, etc.

Different color light indicators on the sensor pad and remote monitor can indicate the occurrence of heartbeats, breathing, and motion sounds. Indicators for adequate power, proper system function, and within effective transmit/receive range can be incorporated.

The sensor pad or bladder can be formed of rubber sheet having folded, sewn or glued seams or, alternatively, screw or compression clamp closures. Hermetically sealed connector grommets can be used to permit leak-free passage of hydrophone outputs. The pad could also be cast or molded of a suitable material, such as polychloroprene rubber. Internal ribbing or cell structure can be used to prevent complete compression of opposed pad walls under severe loading and to preserve continuous liquid communication of the sensor. In yet another embodiment, the hydrophone or other transducer can be mounted on a threaded screw cap engageable with a plastic through-fitting installed in the flexible pad in watertight engagement. This arrangement facilitates easy removal, inspection and replacement of the hydrophone as well as the pad-contained liquid.

Figure 33:
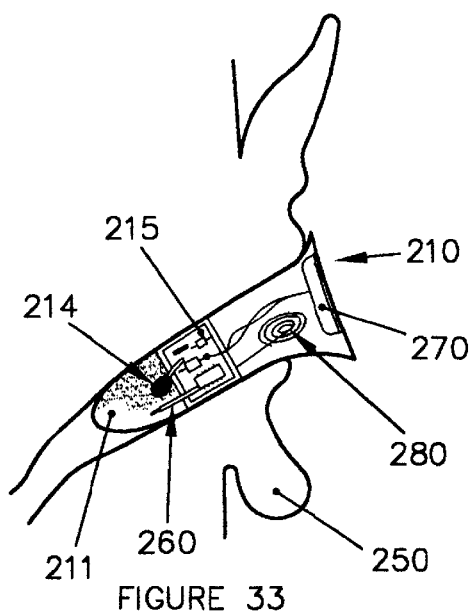
FIG. 33 is a cutaway view of an embodiment of the invention in the form of an earpiece.

FIG. 33 shows the invention in an embodiment designed to fit in an ear. The acoustic monitoring system 210 includes a fluid filled bladder 211 with hydrophone 214 that couples inside an ear 250. Included in the system 210 are electronics 215 for amplifying, filtering, transmitting and receiving signals. The system 210 may optionally include a temperature probe 260 in the fluid or in contact with the skin. Power is supplied by a battery 270. An antenna 280 may be used to transmit and receive signals. The acoustic monitoring system 210 is enclosed in, for example, foam or molded plastic to seal the ear canal from external sounds. The system 210 can monitor heartbeat and breathing.

Figure 34:
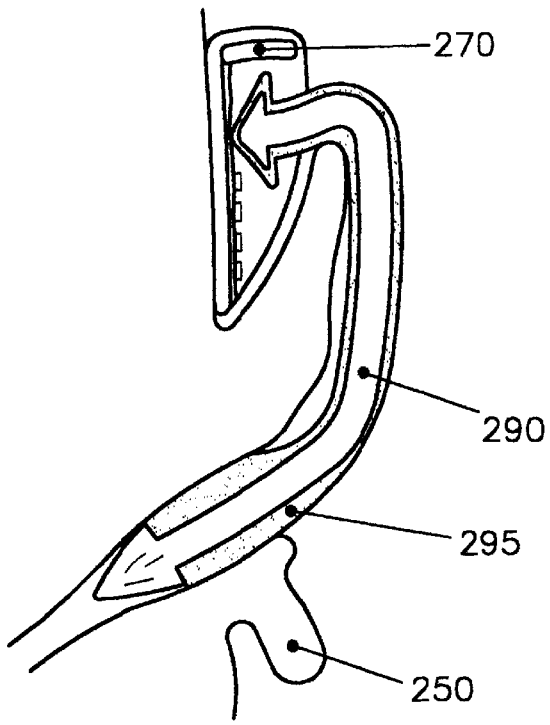
FIG. 34 is a variation of the embodiment of FIG. 33.

FIG. 34 shows a variation of the embodiment of FIG. 33, wherein the hydrophone 214, battery 270 and electronics 215 are mounted outside the ear canal, for example, behind the ear 250. A fluid conduit 290 connects the inner ear with the hydrophone 214. A plug 295 made of, for example, foam, rubber or plastic surrounds the fluid conduit 290 to prevent ambient noise from entering through the fluid conduit walls.

Figure 35:
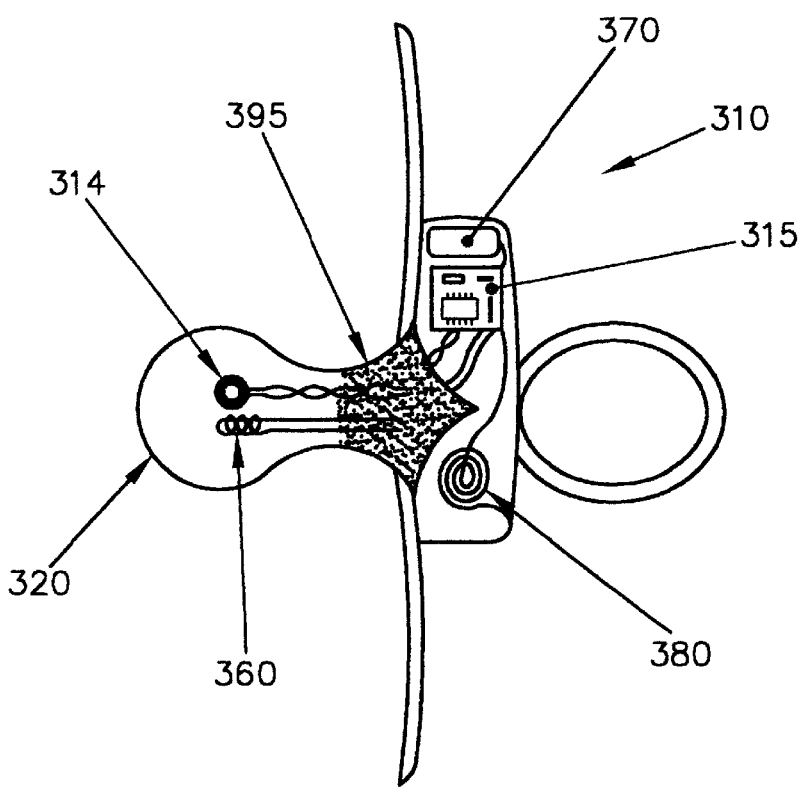
FIG. 35 is a cutaway view of an embodiment of the invention in the form of a pacifier.

FIG. 35 shows an embodiment of the invention in the form of a pacifier 310. The nipple 320 is made of standard nipple material, is fluid filled and houses a hydrophone 314. The pacifier 310 includes electronics 315, battery 370, transmitter 380, optional thermometer 360 and noise isolation material 395. The pacifier 310 can be used to monitor breathing and sucking sounds as an indication of a child's well-being.

Inasmuch as the present invention is subject to many variations, modifications and changes in detail, it is intended that the subject matter discussed above and shown in the accompanying drawings be interpreted as illustrative and not in a limiting sense.

What is claimed is:

1. An acoustic monitoring system comprising:
    a sensor pad adapted to conform to at least a portion of the surface of a living organism, said pad defining at least one chamber containing acoustic transmission material and adapted to receive acoustic signals originating from and produced by the organism; and
    acoustic transducing means coupled with said pad for monitoring and converting said acoustic signals received by said pad to electrical signals corresponding to said acoustic signals.

2. An acoustic monitoring system comprising:
    a sensor pad adapted to conform to at least a portion of the surface of a living organism, said pad defining a plurality of fluid-filled chambers adapted to receive acoustic signals from the organism; and
    acoustic transducing means coupled with said pad for monitoring and converting acoustic signals received by said pad to electrical signals corresponding to said acoustic signals.

3. The acoustic monitoring system of claim 2 wherein said acoustic transducing means includes a plurality of acoustic transducers disposed within respective fluid-filled chambers of said pad.

4. The acoustic monitoring system of claim 2 wherein said acoustic transducing means includes an acoustic transducer communicating with each of said fluid-filled chambers.

5. The acoustic monitoring system of claim 1 further comprising means for transmitting said electrical signals for remote monitoring.

6. The acoustic monitoring system of claim 1 further comprising means for visually displaying said acoustic signals from the organism.

7. The acoustic monitoring system of claim 1 further comprising means for audibly displaying said acoustic signals from the organism.

8. The acoustic monitoring system of claim 1 further comprising a conduit containing acoustic transmission material, for communicating said acoustic signals to said acoustic transducing means, said acoustic transducing means being located within said fluid-filled conduit a predetermined distance from said pad.

9. The acoustic monitoring system of claim 1 further comprising conduit surfaces formed in said pad to channel said acoustic signals toward said acoustic transducing means.

10. An acoustic monitoring system comprising:
    a sensor pad adapted to conform to at least a portion of the surface of a living organism, said pad defining a fluid-filled chamber adapted to receive acoustic signals from the organism;
    acoustic transducing means coupled with said pad for monitoring and converting acoustic signals received by said pad to electrical signals corresponding to said acoustic signals; and
    means for filtering airborne acoustic noise from said electrical signals corresponding to said acoustic signals.

11. The acoustic monitoring system of claim 10 wherein said filtering means includes an air-mounted microphone.

12. The acoustic monitoring system of claim 10 wherein said filtering means includes an acoustic transducer located in said pad, said acoustic transducer being acoustically isolated from said signals from the organism.

13. An acoustic monitoring system comprising:
    a sensor pad adapted to conform to at least a portion of the surface of a living organism, said pad defining a fluid-filled chamber adapted to receive acoustic signals from the organism;
    acoustic transducing means coupled with said pad for monitoring and converting acoustic signals received by said pad to electrical signals corresponding to said acoustic signals; and
    means to store predetermined patterns of acoustic signals and means to provide a comparison of said predetermined patterns to said acoustic signals from the organism.

14. The acoustic monitoring system of claim 13 further comprising means for stimulating said living organism in response to preselected values of said comparison.

15. The acoustic monitoring system of claim 14 wherein said means for stimulating said living organism produces physical movement in said sensor pad.

16. The acoustic monitoring system of claim 14 wherein said means for stimulating said living organism produces visual signals to said organism.

17. The acoustic monitoring system of claim 14 wherein said means for stimulating said living organism provides audible signals to said organism.

18. The acoustic monitoring system of claim 14 wherein said sensor pad is positioned against a portion of a body of the driver of a vehicle and said stimulating means is activated in response to acoustic signals corresponding to predetermined patterns indicating reduced driver alertness.

19. The acoustic monitoring system of claim 13 further comprising a control circuit activated in response to the results of said acoustic signal pattern comparison.

20. The acoustic monitoring system of claim 19 wherein said sensor pad is positioned adjacent an operator location on a piece of heavy machinery and said control circuit inactivates said machinery in the absence of a predetermined operator acoustic signal.

21. An acoustic monitoring system comprising:
a sensor pad adapted to conform to at least a portion of the surface of a living organism, said pad defining a fluid-filled chamber adapted to receive acoustic signals from the organism; and
acoustic transducing means coupled with said pad for monitoring and converting acoustic signals received by said pad to electrical signals corresponding to said acoustic signals;
wherein said sensor pad is filled with water.

22. An acoustic monitoring system comprising:
a sensor pad adapted to conform to at least a portion of the surface of a living organism, said pad defining a fluid-filled chamber adapted to receive acoustic signals from the organism; and
acoustic transducing means coupled with said pad for monitoring and converting acoustic signals received by said pad to electrical signals corresponding to said acoustic signals;
wherein said acoustic transducing means includes a hydrophone.

23. An acoustic monitoring system comprising:
a sensor pad adapted to conform to at least a portion of the surface of a living organism, said pad defining a fluid-filled chamber adapted to receive acoustic signals from the organism;
acoustic transducing means coupled with said pad for monitoring and converting acoustic signals received by said pad to electrical signals corresponding to said acoustic signals;
and a bed having a body support surface wherein said sensor pad of said acoustic monitoring system is positioned on said body support surface of said bed.

24. An acoustic monitoring system comprising:
a sensor pad adapted to conform to at least a portion of the surface of a living organism, said pad defining a fluid-filled chamber adapted to receive acoustic signals from the organism;
acoustic transducing means coupled with said pad for monitoring and converting acoustic signals received by said pad to electrical signals corresponding to said acoustic signals;
and a pillow having a surface to support a portion of a living organism wherein said sensor pad of said acoustic monitoring system is carried on said support surface of said pillow.

25. An acoustic monitoring system comprising:
a sensor pad adapted to conform to at least a portion of the surface of a living organism, said pad defining a fluid-filled chamber adapted to receive acoustic signals from the organism;
acoustic transducing means coupled with said pad for monitoring and converting acoustic signals received by said pad to electrical signals corresponding to said acoustic signals;
and a blood pressure cuff adapted to pressingly encircle a portion of a living organism wherein said sensor pad of said acoustic monitoring system is carried on said encircling cuff.

26. An acoustic monitoring system comprising:
a sensor pad adapted to conform to at least a portion of the surface of a living organism, said pad defining a fluid-filled chamber adapted to receive acoustic signals from the organism;
acoustic transducing means coupled with said pad for monitoring and converting acoustic signals received by said pad to electrical signals corresponding to said acoustic signals;
and a strap apparatus adapted to support animals during lifting and transporting operations wherein said sensor pad of said acoustic monitoring system is carried on said supporting strap apparatus.

27. An acoustic monitoring system comprising:
a sensor pad adapted to conform to at least a portion of the surface of a living organism, said pad defining a fluid-filled chamber adapted to receive acoustic signals from the organism;
acoustic transducing means coupled with said pad for monitoring and converting acoustic signals received by said pad to electrical signals corresponding to said acoustic signals;
and an exercise apparatus having a body support surface wherein said sensor pad of said acoustic monitoring system is carried on said body support surface of said exercise apparatus.

28. The combination of claim 27 wherein said exercise apparatus is a recumbent bicycle.

29. An acoustic monitoring system comprising:
a sensor pad adapted to conform to at least a portion of the surface of a living organism, said pad defining a fluid-filled chamber adapted to receive acoustic signals from the organism;
acoustic transducing means coupled with said pad for monitoring and converting acoustic signals received by said pad to electrical signals corresponding to said acoustic signals;
and a hat having a headband adapted to press against the head of a wearer wherein said sensor pad of said acoustic monitoring system is carried on said headband of said hat.

30. An acoustic monitoring system comprising:
a sensor pad adapted to conform to at least a portion of the surface of a living organism, said pad defining a fluid-filled chamber adapted to receive acoustic signals from the organism;
acoustic transducing means coupled with said pad for monitoring and converting acoustic signals received by said pad to electrical signals corresponding to said acoustic signals;

and eyeglasses having at least one arm adapted to press against the side of the head of a wearer wherein said sensor pad of said acoustic monitoring system is carried on said eyeglass on said at least one arm.

31. An acoustic monitoring system comprising:

a sensor pad adapted to conform to at least a portion of the surface of a living organism, said pad defining a fluid-filled chamber adapted to receive acoustic signals from the organism;

acoustic transducing means coupled with said pad for monitoring and converting acoustic signals received by said pad to electrical signals corresponding to said acoustic signals;

and a pair of goggles having a support surface adapted to press against the head of a wearer wherein said sensor pad of said acoustic monitoring system is carried on said support surface of said goggles.

32. An acoustic monitoring system comprising:

a sensor pad adapted to conform to at least a portion of the surface of a living organism, said pad defining a fluid-filled chamber adapted to receive acoustic signals from the organism;

acoustic transducing means coupled with said pad for monitoring and converting acoustic signals received by said pad to electrical signals corresponding to said acoustic signals;

and at least one earplug adapted to be pressed into the ear of a wearer wherein said sensor pad of said acoustic monitoring system is incorporated into said at least one earplug.

33. An acoustic monitoring system comprising:

a sensor pad adapted to conform to at least a portion of the surface of a living organism, said pad defining a fluid-filled chamber adapted to receive acoustic signals from the organism;

acoustic transducing means coupled with said pad for monitoring and converting acoustic signals received by said pad to electrical signals corresponding to said acoustic signals;

and a medical transport device having a body support surface wherein said sensor pad of said acoustic monitoring system is carried on said body support surface of said medical transport device.

34. The combination of claim 33 wherein said medical transport device includes a gurney.

35. The combination of claim 33 wherein said medical transport device includes a stretcher.

36. The combination of claim 33 wherein said medical transport device includes a wheelchair.

37. The acoustic monitoring system of claim 1 further comprising adjustable straps attached to said pad, wherein said sensor pad is held in acoustic contact with the living organism by said adjustable straps.

38. The acoustic monitoring system of claim 1 further comprising an adjustable belt attached to said pad, wherein said sensor pad is held in acoustic contact with the living organism by said adjustable belt.

39. The acoustic monitoring system of claim 1 further comprising an adhesive patch, wherein said sensor pad is held in acoustic contact with the living organism by said adhesive patch.

40. An acoustic monitoring system comprising:

a sensor pad adapted to conform to at least a portion of the surface of a living organism, said pad defining a fluid-filled chamber adapted to receive acoustic signals from the organism;

acoustic transducing means coupled with said pad for monitoring and converting acoustic signals received by said pad to electrical signals corresponding to said acoustic signals;

and means for creating a vacuum seal around said sensor pad, wherein said sensor pad is held in acoustic contact with the living organism by said vacuum seal created around said pad.

41. An acoustic monitoring system comprising:

a sensor pad adapted to conform to at least a portion of the surface of a living organism, said pad defining a fluid-filled chamber adapted to receive acoustic signals from the organism;

acoustic transducing means coupled with said pad for monitoring and converting acoustic signals received by said pad to electrical signals corresponding to said acoustic signals;

wherein said pad includes a concave vessel having an open side forming a chamber, a substantially acoustically transparent diaphragm extending across said open side and enclosing a volume within said chamber, said chamber being fluid-filled to receive acoustic signals from the organism through said diaphragm.

42. The acoustic monitoring system of claim 41 wherein said chamber is hemispheric in shape.

43. The acoustic monitoring system of claim 41 wherein said chamber is parabolic in shape.

44. The acoustic monitoring system of claim 41 wherein said chamber is formed in a first end of an elongate handheld device for pressing against a body portion of a living organism and further comprising an earphone attached to a second end of said elongate device for audibly monitoring acoustic signals from the organism.

45. An acoustic monitoring system comprising:

a sensor pad adapted to conform to at least a portion of the surface of a living organism, said pad defining a fluid-filled chamber adapted to receive acoustic signals from the organism;

acoustic transducing means coupled with said pad for monitoring and converting acoustic signals received by said pad to electrical signals corresponding to said acoustic signals; and means for transmitting said acoustic signals for remote monitoring;

wherein said sensor pad and acoustic transducing means are miniaturized and included within a swallowable capsule for monitoring internal acoustic signals.

46. An acoustic monitoring system comprising:

a conformable fluid-filled sensor pad;

acoustic transducing means for monitoring and converting acoustic signals received by said sensor pad to electrical signals corresponding to said acoustic signals;

processing means connected to said acoustic transducing means and adapted to receive said electrical signals from said acoustic transducing means;

a transmitter located at a first position and connected to said processing means, said transmitter configured to transmit signals corresponding to the received acoustic signals; and a receiver located at a second position spaced apart from said first position and configured to receive signals from said transmitter.

47. An acoustic monitoring system comprising:

at least one fluid-filled sensor pad adapted to conform to a portion of the surface of a living organism and to receive acoustic signals from the organism;

acoustic transducing means for monitoring and converting acoustic signals received in each of said at least one sensor pads to electrical signals;

fluid-filled conduit means communicating from each of said at least one sensor pads to said acoustic transducing means; and processing means connected to said acoustic transducing means and adapted to receive said electrical signals from said transducing means.

48. An acoustic monitoring system for insertion in an ear having an ear canal, comprising:

a fluid filled bladder;

a hydrophone disposed in the bladder for creating an electrical signal;

electrical circuitry connected to the hydrophone for at least one of amplifying, filtering, transmitting and receiving the electrical signal;

a battery for powering the electrical circuitry;

an antenna connected to the electrical circuitry; and a seal for sealing the ear canal from external sounds.

49. The system of claim 48, further comprising a temperature probe.

50. The system of claim 48, further comprising a fluid filled conduit configured to be inserted in the ear canal and connected to the bladder, wherein the bladder is disposed outside of the ear canal.

51. An acoustic monitoring system, comprising:

a pacifier having a nipple;

fluid and a hydrophone disposed in the nipple, the hydrophone creating an electrical signal;

electrical circuitry connected to the hydrophone for at least one of amplifying, filtering, transmitting and receiving the electrical signal;

a battery for powering the electrical circuitry;

an antenna connected to the electrical circuitry; and noise isolation material for isolating the nipple from a remainder of the pacifier.

52. The system of claim 51, further comprising a temperature probe disposed in the nipple.

53. An acoustic monitoring system comprising:

a sensor pad adapted to conform to at least a portion of the surface of an inanimate object, said pad defining a chamber containing acoustic transmission material and adapted to receive acoustic signals originating from the inanimate object; and acoustic transducing means coupled with said pad for monitoring and converting said acoustic signals received by said pad to electrical signals corresponding to said acoustic signals.

54. The acoustic monitoring system of claim 1 wherein said pad defines a plurality of chambers containing acoustic transmission material.

55. The acoustic monitoring system of claim 54 wherein said acoustic transducing means includes a plurality of acoustic transducers disposed within respective chambers of said pad.

56. The acoustic monitoring system of claim 54 wherein said acoustic transducing means includes an acoustic transducer communicating with each of said chambers.

57. The acoustic monitoring system of claim 1 further comprising means for filtering airborne acoustic noise from said electrical signals corresponding to said acoustic signals.

58. The acoustic monitoring system of claim 1 further comprising a second acoustic monitoring system as set forth in claim 1 wherein the sensor pads are located on different areas of the organism.

59. The acoustic monitoring system of claim 58 wherein at least one of the acoustic transducing means includes a filtering means for acoustically isolating the at least one acoustic transducing means from at least one of the signals of the organism.

60. The acoustic monitoring system of claim 1 further comprising means to store predetermined patterns of acoustic signals and means to provide a comparison of said predetermined patterns to said acoustic signals from the organism.

61. The acoustic monitoring system of claim 60 further comprising means for stimulating said living organism in response to preselected values of said comparison.

62. The acoustic monitoring system of claim 61 wherein said means for stimulating said living organism produces physical movement in said sensor pad.

63. The acoustic monitoring system of claim 61 wherein said means for stimulating said living organism produces visual signals to said organism.

64. The acoustic monitoring system of claim 61 wherein said means for stimulating said living organism provides audible signals to said organism.

65. The acoustic monitoring system of claim 61 wherein said sensor pad is configured to be positioned against a portion of the body of the driver of a vehicle and said stimulating means is configured to be activated in response to acoustic signals corresponding to predetermined patterns indicating reduced driver alertness.

66. The acoustic monitoring system of claim 60 further comprising a control circuit activated in response to the results of said acoustic signal pattern comparison.

67. The acoustic monitoring system of claim 66 wherein said sensor pad is configured to be positioned adjacent the operator location on a piece of machinery and said control circuit inactivates said machinery in the absence of a predetermined operator acoustic signal.

68. The acoustic monitoring system of claim 1 further comprising an article of clothing wherein said sensor pad is attached to the article of clothing.

69. The acoustic monitoring system of claim 1 further comprising an adjustable band wherein said sensor pad is disposed in said band and said sensor pad is held in contact with said organism by said band.

70. In combination, an acoustic monitoring system as recited in claim 1 and a structure having a body support surface wherein said sensor pad of said acoustic monitoring system is positioned on said body support surface of said structure.

71. In combination, an acoustic monitoring system as recited in claim 1 and a pillow having a surface to support a portion of a living organism wherein said sensor pad of said acoustic monitoring system is carried on said support surface of said pillow.

72. In combination, at least one acoustic monitoring system as recited in claim 1 and a blood pressure cuff adapted to pressingly encircle a portion of a living organism wherein at least one sensor pad of said at least one acoustic monitoring system is carried on said encircling cuff.

73. In combination, an acoustic monitoring system as recited in claim 1 and a strap apparatus adapted to support animals during lifting and transporting operations wherein said sensor pad of said acoustic monitoring system is carried on said supporting strap apparatus.

74. In combination, an acoustic monitoring system as recited in claim 1 and an exercise apparatus having a body contact surface wherein said sensor pad of said acoustic monitoring system is carried on said body contact surface of said exercise apparatus.

75. The acoustic monitoring system of claim 1 wherein at least a portion of a surface of the sensor pad includes acoustic insulating material.

76. In combination, an acoustic monitoring system as recited in claim 1 and a headband adapted to press against the head of a wearer wherein said sensor pad of said acoustic monitoring system is carried on said headband.

77. In combination, an acoustic monitoring system as recited in claim 1 and eyewear having at least one arm adapted to press against the side of the head of a wearer wherein said sensor pad of said acoustic monitoring system is carried on said eyewear on said at least one arm.

78. In combination, an acoustic monitoring system as recited in claim 1 and a pair of goggles having a support surface adapted to press against the head of a wearer wherein said sensor pad of said acoustic monitoring system is carried on said support surface of said goggles.

79. In combination, an acoustic monitoring system as recited in claim 1 and at least one earplug adapted to be pressed into the ear of a wearer wherein said sensor pad of said acoustic monitoring system is incorporated into said at least one earplug.

80. In combination, an acoustic monitoring system as recited in claim 1 and a medical transport device having a body support surface wherein said sensor pad of said acoustic monitoring system is one of carried on and built into said body support surface of said medical transport device.

81. The acoustic monitoring system of claim 1 further comprising means for changing a temperature of the sensor pad.

82. The acoustic monitoring system of claim 1 further comprising means for transmitting one of the acoustic and electrical signals to a telephone.

83. The acoustic monitoring system of claim 1 further comprising a thermometer.

84. The acoustic monitoring system of claim 1 further comprising means for creating a vacuum seal around said sensor pad, wherein said sensor pad is held in acoustic contact with the living organism by said vacuum seal created around said pad.

85. The acoustic monitoring system of claim 1 wherein said pad includes a concave vessel having an open side forming a chamber, a substantially acoustically transparent diaphragm extending across said open side and enclosing a volume within said chamber, said chamber containing acoustic transmission material to receive acoustic signals from the organism through said diaphragm.

86. The acoustic monitoring system of claim 1 further comprising a global positioning system.

87. The acoustic monitoring system of claim 1 further comprising means for transmitting the electrical signals to electrical equipment.

88. The acoustic monitoring system of claim 85 wherein said chamber is formed in a first end of a hand-held device for pressing against a body portion of a living organism and further comprising an earphone attached to a second end of said device for audibly monitoring acoustic signals from the organism.

89. The acoustic monitoring system of claim 5 wherein said sensor pad and acoustic transducing means are miniaturized and included within a swallowable capsule for monitoring internal acoustic signals.

90. An acoustic monitoring system comprising:
a conformable sensor pad containing acoustic transmission material;
acoustic transducing means for monitoring and converting acoustic signals received by said sensor pad to electrical signals corresponding to said acoustic signals;
processing means connected to said acoustic transducing means and adapted to receive said electrical signals from said acoustic transducing means;
a transmitter located at a first position and connected to said processing means, said transmitter configured to transmit signals corresponding to the received acoustic signals; and
a receiver located at a second position spaced apart from said first position and configured to receive signals from said transmitter.

91. An acoustic monitoring system comprising:
at least one sensor pad containing acoustic transmission material and adapted to conform to a portion of the surface of a living organism and to receive acoustic signals from the organism;
acoustic transducing means for monitoring and converting acoustic signals received in each of said at least one sensor pads to electrical signals;
conduit means containing acoustic transmission material and communicating from each of said at least one sensor pads to said acoustic transducing means; and
processing means connected to said acoustic transducing means and adapted to receive said electrical signals from said transducing means.

92. An acoustic monitoring system for insertion in an ear having an ear canal, comprising:
a bladder containing acoustic transmission material;
a hydrophone disposed in the bladder for creating electrical and acoustic signals;
electrical circuitry connected to the hydrophone for at least one of amplifying, filtering, transmitting and receiving the electrical signal;
a battery for powering the electrical circuitry;
an antenna connected to the electrical circuitry; and
a seal for sealing the ear canal from external sounds.

93. The system of claim 92, further comprising a temperature probe.

94. The system of claim 92, further comprising a conduit containing acoustic transmission material and inserted in the ear canal and connected to the bladder, wherein the bladder is disposed outside of the ear canal.

95. An acoustic monitoring system, comprising:
a pacifier having a nipple;
acoustic transmission material and a hydrophone disposed in the nipple, the hydrophone creating an electrical signal;
electrical circuitry connected to the hydrophone for at least one of amplifying, filtering, transmitting and receiving the electrical signal;
a battery for powering the electrical circuitry;
an antenna connected to the electrical circuitry; and
noise isolation material for isolating the nipple from a remainder of the pacifier.

96. The acoustic monitoring system of claim 1, further comprising internal supports in the sensor pad.

* * * * *

Disclaimer 5,853,005—Michael V. Scanlon, Silver Spring, Md. ACOUSTIC MONITORING SYSTEM. Patent dated December 29, 1998. Disclaimer filed November 14, 2000, by the assignee, The United States of America as represented by the Secretary of the Army.

Hereby enters this disclaimer to claims 1, 2, 5, 6, 7, 13, 19, 21, 22, 23, 24, 46, 47, 53, 54, 58, 60, 66, 70, 71, 75, 82, 87, 90 and 91 of said patent.

(*Official Gazette*, January 16, 2001)